(12) United States Patent
Rey et al.

(10) Patent No.: US 6,309,872 B1
(45) Date of Patent: Oct. 30, 2001

(54) POLYPEPTIDES HAVING GLUCOAMYLASE ACTIVITY AND NUCLEIC ACIDS ENCODING SAME

(75) Inventors: Michael W. Rey; Elizabeth J. Golightly, both of Davis, CA (US)

(73) Assignee: Novozymes Biotech, Inc, Davis, CA (US)

( * ) Notice: Subject to any disclaimer, the term of this patent is extended or adjusted under 35 U.S.C. 154(b) by 0 days.

(21) Appl. No.: 09/704,449

(22) Filed: Nov. 1, 2000

(51) Int. Cl.[7] .................................................... C12N 9/34

(52) U.S. Cl. ............................................ 435/205; 536/23.2
(58) Field of Search .............................. 435/205, 254.11; 536/23.2

*Primary Examiner*—Nashaat T. Nashed
*Assistant Examiner*—Malgorzata A. Walicka
(74) *Attorney, Agent, or Firm*—Robert L. Starnes

(57) ABSTRACT

The present invention relates to isolated polypeptides having glucoamylase activity and isolated nucleic acid sequences encoding the polypeptides. The invention also relates to nucleic acid constructs, vectors, and host cells comprising the nucleic acid sequences as well as methods for producing and using the polypeptides.

12 Claims, 17 Drawing Sheets

```
TCTAGAAGACGGTACCATTGCCATTCGGCCCTTCCTAAGCGGCTGGTGTCGGAATAAGCTTTCGGCCCCCACGGATACCCC    80
ATAACTATCCTGGGCCGACATCATCTGTACTCGACAGACTGCTTATCGTCTTATCCCAGGTGCGGGGCC             160
CCGCAGGCCGAGTCGGAGCCGGTGCCGGTGCTCCAGTTCTCTCGAGCTTATGGCTTCCACGCAGCTTCGCACCGGCCGTCT    240
GGCTCCATATTCCCCATATAAAGACATGTGATCGTTTCCACGTCCAGCAGCATGCGCCGTCCAGCAGCTCTTATGGCTCTTCAGCTCTTCAGCTCTTCGGCCTCTTATTGGCCCTGCTTCCTGCTGC    320
CAACTTCTCGGCTTGATCGTTTTCCACGTCCAGCAGCATGCGCCGTCCAGCAGCTCTTATGGCTCTTCAGCTCTTCGGCCTCTTATTGGCCCTGCTTCCTGCTGC    400
                                  M R R L Q L L G L L A L L P A A
GCTCGGCCATCCGGAGGCTAGCCGTGTCCGGCGAGGGGGAGGTGGTGAAGAGGTCTGTCATCGCCTTCATCGCCACCG       480
 L G H P E A S R V R R E G E V V K R S V D S F I A T
AGAGCCCATTGCCTTGTCCAACTGCTCTGTAACATCGGCTCTCGCGCCATGCTTCGGCGTCCTCGGCGCTCGGCCTCGGGTATC 560
 E S P I A L S N L C N I G S T G C H A S G V A S G I
GTCGTTGCGTCTCCCCGGACAAGAACCCGGACTGTATGTGCACTCGGCCTCTCTTCCCGCCGCTGTTCGCAGGCTAAC      640
 V V A S P D K T N P
DTTGTACAGACTGTATACTTGGACTAGAGACAGGCGCTCACCTTCAAGTGCGTTGTCGACACCTTCACCAACAGTACG       720
     Y W Y T W T R D S A L T F K C V V D T F T N S Y
ATGCCTCGCTCCAGGCCGAGATCCAGAACTACATCGTCGCGCAGGCCCATCTGCAGGGCGTCTCGAACCCGTCCGGCAGC    800
 D A S L Q A E I Q N Y I V A Q A H L Q G V S N P S G S
CTCTCGGACGGTTCCGGCCTGGGAGAACCCAAGTTCAACGTCGACAATGAGCCAGTTCACGGCGCTGGGTATGTCTTTG    880
 L S D G S G L G E P K F N V D M S Q F T G A W
CAAGGCCCACGCCCTGACACTGTCTCCCCGTTTCATTATCCTGACCAGCAACAGGTACAGAGAGACGGTCCGGCTC       960
                                            G R P Q R D G P A
TCCGGGGCGATCGCCCTGATCGCTTACTCAAAGTGGCTTCAAAGTGGCTGATCAGCAACTTCGACTTCGAGCATGCGTCTGG  1040
 L R A I A L I A Y S K W L I S N G Y T S T A S S I V W
CCCGTCATCAAGAACGATCTGGCATAGCTGCCCAGTACGTTGCTGATCCGTCAATGTGCTGAGAGGGC              1120
 P V I K N D L A Y V A Q
GACCGGCTGACATTCATCCCTTTCATACAGGAACAACACAGGTTTCGATCTTTGGGAGGAAGTCTCTGGCAGTTCCTTCT   1200
 N N T G F D L W E E V S G S S F
TCACGGTGCGCCAACCAACAGAGAGTACGGCGGATATCAAAGTGACAAATCAAAGTGCCTGCTGACGTCGACTGGTG     1280
 F T V A N Q H R
GCCCGTAGCATTGGTGGAGGTGCCAGCTTCTGCAGAGCTTCTGTGCGCCTTCCAGTGCCTCTGCCGTCGCCGCCC        1360
 A L V E G A A L A T S L G T S C S A V A P
AGATCCTGTGCTTCCTGCAGAGTGCAGGGTTGTCGGTGGTGCTAACAAAATCAAGTCAACGAGAACAACGGCCGCCAAGGACGCGA 1440
 Q I L C F L Q S F W S P S S G Y I L A N S T
TATCGCACAGTGCAGGGTTGTCGGTGGTGCTAACAAAATCAAGTCAACGAGAACAACGGCCGCCAAGGACGCGA           1520
                                                          A K D A
```

Fig. 1A

```
ACACATTGCTGGGCTCGATTCACACGTTTGATCCCGCGCGGCTGCGACGCGGCGACTTTCCAGCCCTGCAGTGACCGG  1600
 N  T  L  L  G  S  I  H  T  F  D  P  A  A  G  C  D  A  A  T  F  Q  P  C  S  D  R
GCGCTGGCCAACCACAAGTCGTGACCGACGCGTTCCGGTCCATCTACTCCATCAACTCCGGCATTGCCGAGGGCAGCGC  1680
 A  L  A  N  H  K  V  V  T  D  A  F  R  S  I  Y  S  I  N  S  G  I  A  E  G  S  A
CGTCGCGGTCGGCCGCTATCCCGAGGACAGCTACTTCGGCGGCAACCCCTGTACCTCAACACACTGGCCGCCGAGC    1760
 V  A  V  G  R  Y  P  E  D  S  Y  F  G  G  N  P  W  Y  L  N  T  L  A  A  E
AGCTGTACGATGCCCTCTACGTCTGGAAGAAGCAGGGCTCCATCACCATCGACGTCGCTGGCCTTCTTCAAAGAC    1840
 Q  L  Y  D  A  L  Y  V  W  K  K  Q  G  S  I  T  V  T  S  L  A  F  F  K  D
TTCTCTCGTCCATCACCCCGGGCACGTACTCCTCCAGCACGTACACAACCCTGTACAACGCCATCTCGGCGTA      1920
 F  S  S  S  I  T  P  G  T  Y  S  S  S  T  Y  T  T  L  Y  N  A  I  S  A  Y
CGCCGACGGCTACATGAACATCGTCGCCCAGTACGCCAGACCAACGGCTCGTGCGAGCAGTTCTCCAAGACCAACG    2000
 A  D  G  Y  M  N  I  V  A  Q  Y  A  Q  T  N  G  S  L  S  E  Q  F  S  K  T  N
GCGAGCCGCTCTCCGGGGCGCTCTACGACCTGACCTGGTCCTACGCGGCCTTCCTCACGGCCAGCGCCCGGCGTCGTG  2080
 G  E  P  L  S  A  Y  D  L  T  W  S  Y  A  A  F  L  T  A  A  R  R  A  G  V  V
CCCCCTCCTGGGGCGCGGCCAGCAACAGCGTCCCGGCCAACAGCGTCTCCGCCACCTCCGTCGTCGGCTCCTACACCTC  2160
 P  P  S  W  G  A  A  S  A  N  S  V  P  A  Q  C  S  A  T  S  V  V  G  S  Y  T  S
CGCCAGCGCGACCTCCTTCCCGCCGAGCCAGACCCCCGCCGTCTGGGACACCAGCAAGGCCGTGCCGCTCAGCGCCGCC  2240
 A  T  S  F  P  P  S  Q  T  P  A  S  S  T  S  A  G  S  S  P  A  S  S  T
CCGCCACCACCGCCTCACCTTCAACGAGCGCGTGACCACCCAGTGGGGCCAG                           2320
 T  A  T  A  T  A  C  S  T  P  T  A  V  T  F  N  E  R  V  T  T  Q  W  G  Q
ACGATCAAGGTGGTCGGCGACGCCGCCGCGCTCGGCGGCTGGGACACCAGCAAGGCCGTGCCGCTCAGCGCCGCC    2400
 T  I  K  V  V  G  D  A  A  A  L  G  G  W  D  T  S  K  A  V  P  L  S  A  A  G  Y
CACCGCCAGCGACCCGCTGTGGTCGGGCACCGTCGACCTGCCCGCCGGGCTCGCCGTCCAGTACAAGTACATCAACGTGG 2480
 T  A  S  D  P  L  W  S  G  T  V  D  L  P  A  G  L  A  V  Q  Y  K  Y  I  N  V
CGGCCGACGGGGGCGTCACGTGGGAGGCGGATCCGAATCATTCGTTTACGGTGCCTGCGGTGCGGACCACGGCGGTA    2560
 A  A  D  G  G  V  T  W  E  A  D  P  N  H  S  F  T  V  P  A  A  C  G  T  T  A  V
ACCAGGGATGATACCTGGCAGTAAATTCGAGGATGGGGTTGGGGAGGTGGTGGTGGAGGTTGTTGGCGTGTGGCGGTGG  2640
 T  R  D  D  T  W  Q
GATGGGATGTAGGGTTGAATGGGAGGTGCCCAAGCAAGTGTCAACGAAGTGTCTATTCTGATGACGATTGATTCTTCT  2720
GTATATAGTTCTTATGAAGTTGTATGTACTTGACATGATGATGTCCTTGCTTCAATATGCATTCTGCTCGGGA       2800
GTTGAAAATTAGTTCATGCTTCATATTGGTGGCCATTGACGACCTGAACGAAGACCATGACGTTGGCCTCAATCA     2880
CTTTCATATCGGCAAGAGATCGATAGGGGAGCCTGCTATTGTACCCGCAAGAAACCCTTTCTCCCACTTCGTC       2960
ACCATCAAGAGCCCCCTCGACATCCTCCCGGGACTTTGCCGTGACGAGACTCAGGATGCAGTTACACCCGACATGCTCC  3040
GGCGGCAGCACGCTCTGTAGACATCCCCGAGACATTCAAGTACCCGACGCGCCCTTATCCAACCG               3120
AAAGATGGCGTGGTCCACCAGCGCGTAGGTGCCGGGCACGATCATCTCCATATCCACGATGGTGCCGCCCGGG       3196
```

POLYPEPTIDES HAVING GLUCOAMYLASE ACTIVITY AND NUCLEIC ACIDS ENCODING SAME

BACKGROUND OF THE INVENTION

1. Field of the Invention

The present invention relates to isolated polypeptides having glucoamylase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

High dextrose and fructose syrups are made by enzymatic saccharification of liquefied starch. The saccharification is achieved by means of a dextrose-forming exo-amylase known as exo-1,4-alpha-D-glucosidase (glucoamylase or amylogulcosidase). The enzyme hydrolyzes 1,4-as well as 1,6-alpha-linkages in starch. During hydrolysis, glucose units are removed in a step-wise manner from the non-reducing ends of the substrate molecule, whereas the 1,6-alpha-linkages found in branched dextrins are broken down relatively slowly. Maltotriose and maltose are hydrolyzed at a lower rate than higher oligosaccharides. Glucoamylases are also used to lower the carbohydrate content of beer.

*Thielavia terrestris* is a thermophilic filamentous fungus that can grow at low pH of 4.5 and elevated temperature of 40–45° C. (WO 96/02653). The ascomycete has a wide geographic distribution and a homothallic mating behavior (Mouchacca, 1997, *Cryptogamie Mycol.* 18: 19–69). Several enzymes are known to be produced by Thielavia including xylanase, glucanase, cellulase, glucosidase, mannanase, and galactanase.

There is a need in the art for new sources of glucoamylase with improved properties of thermostability.

It is an object of the present invention to provide improved polypeptides having glucoamylase activity and nucleic acid encoding the polypeptides.

SUMMARY OF THE INVENTION

The present invention relates to isolated polypeptides having glucoamylase activity selected from the group consisting of:

(a) a polypeptide having an amino acid sequence which has at least 75% identity with amino acids 20 to 630 of SEQ ID NO:2;

(b) a polypeptide encoded by a nucleic acid sequence which hybridizes under high stringency conditions with (i) nucleotides 411 to 2581 of SEQ ID NO:1, (ii) the cDNA sequence contained in nucleotides 411 to 2581 of SEQ ID NO:1, (iii) a subsequence of (i) or (ii) of at least 100 nucleotides, or (iv) a complementary strand of (i), (ii), or (iii);

(c) a variant of the polypeptide having an amino acid sequence of SEQ ID NO:2 comprising a substitution, deletion, and/or insertion of one or more amino acids;

(d) a fragment of (a) or (b) that has glucoamylase activity; and (f) a polypeptide having with physicochemical properties of (i) a pH optimum in the range between about pH 3 and about pH 7, determined at 20° C. in the presence of maltotriose; (ii) a temperature optimum in the range of from about 20° C. to about 70° C., determined at pH 4 in the presence of maltotriose; and (iii) a residual activity of 32%, relative to initial activity, at pH 4.3 after 20 minutes at 70° C. in the absence of maltotriose.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIG. 1 shows the genomic DNA sequence and the deduced amino acid sequence of a *Thielavia terrestris* ATCC 20627 glucoamylase (SEQ ID NOS:1 and 2, respectively).

DETAILED DESCRIPTION OF THE INVENTION

Polypeptides Having Glucoamylase Activity

Figure 2:
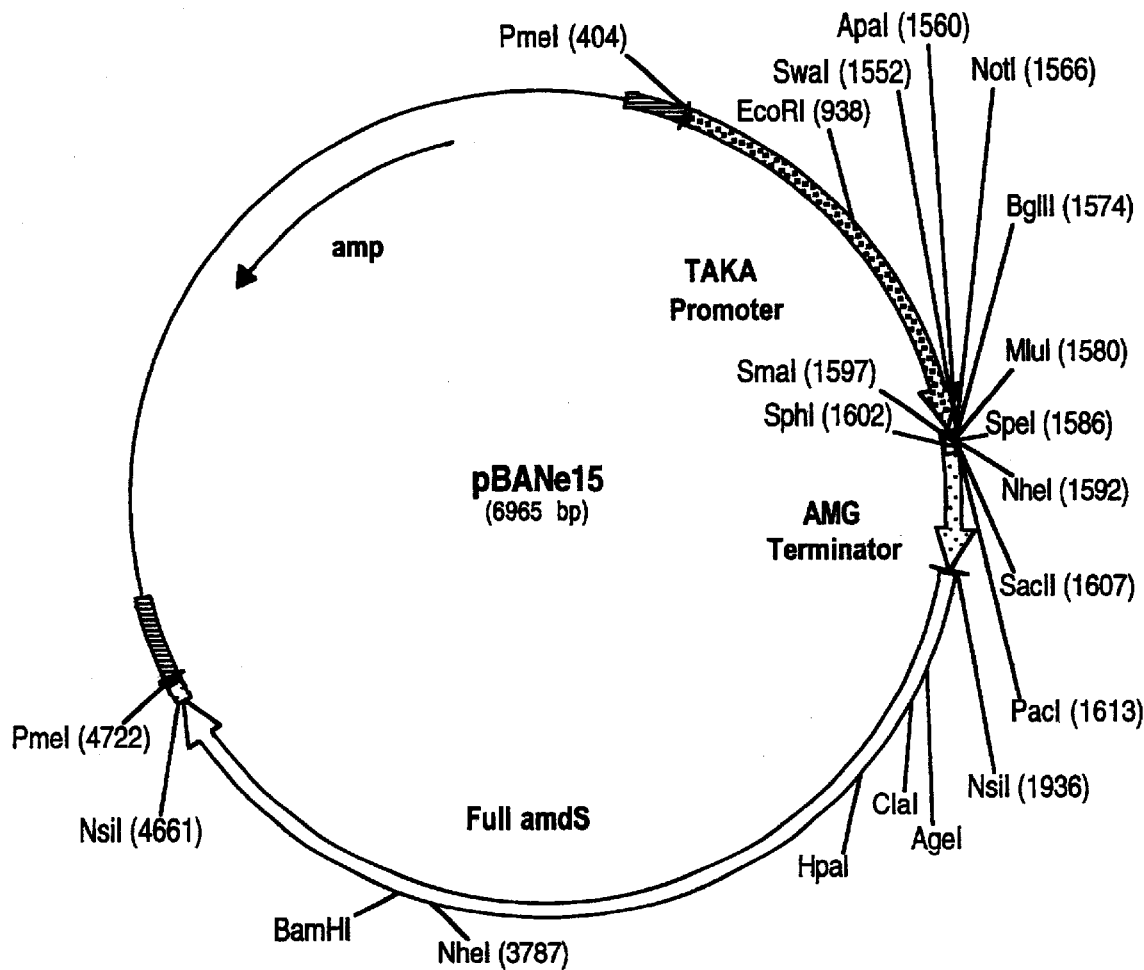
FIG. 2 shows a restriction map of pBANe15.

The term "glucoamylase activity" is defined herein as a dextrin 6-alpha-D-glucanohydrolase activity which catalyses the endohydrolysis of 1,6-alpha-D-glucoside linkages at points of branching in chains of 1,4-linked alpha-D-glucose residues. For purposes of the present invention, glucoamylase activity is determined according to the procedure described by Fagershom and Kalkkinen, 1995, *Biotechnol. Appl. Biochem.* 21: 223–231, where the glucose produced by the glucoamylase from 0.1 M maltotriose is measured using a GO glucose oxidase assay kit (Sigma Chemical Co., St. Louis, Mo.) at pH 4, 25° C. One unit of glucoamylase activity is defined as 1.0 mole of glucose produced per minute at 25° C., pH 4.

In a first embodiment, the present invention relates to isolated polypeptides having an amino acid sequence which has a degree of identity to amino acids 20 to 630 of SEQ ID NO:2 (i.e., the mature polypeptide) of at least about 75%, preferably at least about 80%, more preferably at least about 85%, even more preferably at least about 90%, most preferably at least about 95%, and even most preferably at least about 97%, which have glucoamylase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 20 to 630 of SEQ ID NO:2. For purposes of the present invention, the degree of identity between two amino acid sequences is determined by the ClustalW method (Higgins, 1989, *CABIOS* 5: 151–153; Thompson et al., 1994, *Nucleic Acids Research* 22: 4673–4680; Thompson et al., 1997, *Nucleic Acids Research* 25: 4876–4882) using the LASERGENE™ MEGALIGN™ software (DNASTAR, Inc., Madison, Wis.) with a blosum weight matrix and gap extension penalty of 0.03 to 0.05 and the following multiple alignment parameters: Gap penalty of 10 and gap length penalty of 10. Pairwise alignment parameters were Ktuple=1, gap penalty=3, windows=5, and diagonals=5.

Preferably, the polypeptides of the present invention comprise the amino acid sequence of SEQ ID NO:2 or an allelic variant thereof; or a fragment thereof that has glucoamylase activity. In a more preferred embodiment, the polypeptide of the present invention comprises the amino acid sequence of SEQ ID NO:2. In another preferred embodiment, the polypeptide of the present invention comprises amino acids 20 to 630 of SEQ ID NO:2, or an allelic variant thereof; or a fragment thereof that has glucoamylase activity. In another preferred embodiment, the polypeptide of the present invention comprises amino acids 20 to 630 of SEQ ID NO:2. In another preferred embodiment, the polypeptide of the present invention consists of the amino acid sequence of SEQ ID NO:2 or an allelic variant thereof; or a fragment thereof that has glucoamylase activity. In another preferred embodiment, the polypeptide of the present invention consists of the amino acid sequence of SEQ ID NO:2. In another preferred embodiment, the polypeptide consists of amino acids 20 to 630 of SEQ ID NO:2 or an allelic variant thereof, or a fragment thereof that has glucoamylase activity. In another preferred embodiment, the polypeptide consists of amino acids 20 to 630 of SEQ ID NO:2.

A fragment of SEQ ID NO:2 is a polypeptide having one or more amino acids deleted from the amino and/or carboxyl terminus of this amino acid sequence. Preferably, a fragment contains at least 550 amino acid residues, more preferably at least 570 amino acid residues, and most preferably at least 590 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having glucoamylase activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 411 to 2581 of SEQ ID NO:1, (ii) the cDNA sequence contained in nucleotides 411 to 2581 of SEQ ID NO:1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO:1 may be at least 100 nucleotides or preferably at least 200 nucleotides. Moreover, the subsequence may encode a polypeptide fragment which has glucoamylase activity. The polypeptides may also be allelic variants or fragments of the polypeptides that have glucoamylase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having glucoamylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having glucoamylase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is the mature polypeptide coding region of SEQ ID NO:1. In another preferred embodiment, the nucleic acid probe is the nucleic acid sequence contained in plasmid pEJG72/XL1Blue which is contained in *Escherichia coil* NRRL B-30358, wherein the nucleic acid sequence encodes a polypeptide having glucoamylase activity. In another preferred embodiment, the nucleic acid probe is the mature polypeptide coding region contained in plasmid pEJG72/XL1Blue which is contained in *Escherichia coli* NRRL B-30358.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO:2 comprising a substitution, deletion, and/or insertion of one or more amino acids.

The amino acid sequences of the variant polypeptides may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having the following physicochemical properties: (i) a pH optimum in the range between about pH 3 and about pH 7, preferably between about pH 3 and about pH 6, more preferably between about pH 4 and about pH 6, and most preferably between about pH 4 and about pH 5, determined at 20° C. in the presence of maltotriose; (ii) a temperature optimum in the range of from about 20° C. to about 70° C., more preferably about 30° C. to about 60° C., and most preferably about 50° C. to about 60° C., determined at pH 4 in the presence of maltotriose; and (iii) a residual activity of 32%, relative to initial activity, at pH 4.3 after 20 minutes at 70° C. in the absence of maltotriose. The Thielavia glucoamylase has a residual activity of 32% after 20 minutes at pH 4.3, 70° C, while *Aspergillus niger* glucoamylase has a residual activity of 18%. Thus, the Thielavia glucoamylase is 178% more stable than the *Aspergillus niger* glucoamylase. The $K_m$ is <1 mM at pH 4 from 4° C. to 80° C. and from pH 3 to 11 at 20° C. The $k_{cat}$ is >$10^5$/min at pH 4 from 40° C. to 70° C., and from pH 3 to 7 at 20° C.

In a fifth embodiment, the present invention relates to isolated polypeptides having immunochemical identity or partial immunochemical identity to the polypeptide having the amino acid sequence of SEQ ID NO:2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the glucoamylase activity of the mature polypeptide of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred embodiment, the polypeptide is a *Thielavia achromatica, Thielavia albomyces, Thielavia albopilosa, Thielavia appendiculata, Thielavia arenaria, Thielavia australiensis, Thielavia basicola, Thielavia californica, Thielavia fimeti, Thielavia fragilis, Thielavia heterothallica, Thielavia hyrcaniae, Thielavia kirilenkoae, Thielavia kiwaitensis, Thielavia leptoderma, Thielavia microspora, Thielavia minuta, Thielavia octospora, Thielavia ovispora, Thielavia peruviana, Thielavia sepedonium, Thielavia setosa, Thielavia spirotricha, Thielavia subthermophila, Thielavia tanzanica, Thielavia terrestris, Thielavia terricola, Thielavia tetraspora, Thielavia thermophila, Thielavia tortuosa, Thielavia variospora,* or *Thielavia wareingii* polypeptide.

In a more preferred embodiment, the polypeptide is a *Thielavia terrestris* polypeptide, and most preferably a *Thielavia terrestris* ATCC 20627 polypeptide, e.g., the polypeptide with the amino acid sequence of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of Thielavia are defined by Morgan-Jones, 1974, *Canadian Journal of Botany* 52: 429–431; and Glenn et al., 1996, *Mycologia* 88: 369–38. For instance, the imperfect form of *Thielavia terrestris* is known as *Acremonium alabamense*.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-glucoamylase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set 15–4 forth in SEQ ID NO:1. In another more preferred embodiment, the nucleic acid sequence is the sequence contained in plasmid pEJG72/XL1Blue that is contained in *Escherichia coli* NRRL B-30358. In another preferred embodiment, the nucleic acid sequence is the mature polypeptide coding region of SEQ ID NO:1. In another more preferred embodiment, the nucleic acid sequence is the mature polypeptide coding region contained in plasmid pEJG72/XL1Blue that is contained in *Escherichia coli*

NRRL B-30358. The present invention also encompasses nucleic acid sequences which encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 which encode fragments of SEQ ID NO:2 that have glucoamylase activity. A subsequence of SEQ ID NO:1 is a nucleic acid sequence encompassed by SEQ ID NO:1 except that one or more nucleotides from the 5' and/or 3' end have been deleted. Preferably, a subsequence contains at least 1650 nucleotides, more preferably at least 1710 nucleotides, and most preferably at least 1770 nucleotides.

The present invention also relates to mutant nucleic acid sequences comprising at least one mutation in the mature polypeptide coding sequence of SEQ ID NO:1, in which the mutant nucleic acid sequence encodes a polypeptide which consists of amino acids 20 to 630 of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR. *A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Thielavia, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO:1 (i.e., nucleotides 411 to 2581) of at least about 75%, preferably about 80%, preferably about 85%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for glucoamylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 411 to 2581 of SEQ ID NO:1, (ii) the cDNA sequence contained in nucleotides 411 to 2581 of SEQ ID NO:1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has glucoamylase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO:1 or a subsequence thereof, wherein the mutant nucleic acid sequence encodes a polypeptide which consists of amino acids 20 to 630 of SEQ ID NO:2 or a fragment thereof which has glucoamylase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 354 to 410 of SEQ ID NO:1 which encode amino acids 1 to 19 of SEQ ID NO:2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for Bacillus subtilis alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof.

Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC 184 permitting replication in *E. coli*, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication.

The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* and *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus,* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168:111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce the polypeptide; and (b) recovering the polypeptide. Preferably, the strain is of the genus Thielavia, and more preferably *Thielavia terrestris*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO:1, wherein the mutant nucleic acid sequence encodes a polypeptide which consists of amino acids 20 to 630 of SEQ ID NO:2, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having glucoamylase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a Vicia faba promoter from the legumin B4 and the unknown seed protein gene from Vicia faba (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus,* or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art. The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, Science 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having glucoamylase activity of the present invention under conditions conducive for production of the polypeptide; and (b) recovering the polypeptide.

Removal or Reduction of Glucoamylase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced glucoamylase activity may be conveniently accomplished by modification or inactivation of a nucleic acid sequence necessary for expression of the polypeptide having glucoamylase activity in the cell. The nucleic acid sequence to be modified or inactivated may be, for example, a nucleic acid sequence encoding the polypeptide or a part thereof essential for exhibiting glucoamylase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the glucoamylase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced glucoamylase activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of glucoamylase activity by fermentation of a cell which produces both a polypeptide of the present invention as well as the protein product of interest by adding an effective amount of an agent capable of inhibiting glucoamylase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of glucoamylase activity by cultivating the cell under conditions permitting the expression of the product, subjecting the resultant culture broth to a combined pH and temperature treatment so as to reduce the glucoamylase activity substantially, and recovering the product from the culture broth. Alternatively, the combined pH and temperature treatment may be performed on an enzyme preparation recovered from the culture broth. The combined pH and temperature treatment may optionally be used in combination with a treatment with a glucoamylase inhibitor.

In accordance with this aspect of the invention, it is possible to remove at least 60%, preferably at least 75%, more preferably at least 85%, still more preferably at least 95%, and most preferably at least 99% of the glucoamylase activity. Complete removal of glucoamylase activity may be obtained by use of this method.

The combined pH and temperature treatment is preferably carried out at a pH in the range of 3–4 or 8–11 and a temperature in the range of 60–80° C. for a sufficient period of time to attain the desired effect, where typically, to 60 minutes is sufficient.

The methods used for cultivation and purification of the product of interest may be performed by methods known in the art.

The methods of the present invention for producing an essentially glucoamylase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The glucoamylase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from glucoamylase activity which is produced by a method of the present invention.

Compositions

In a still further aspect, the present invention relates to compositions comprising a polypeptide of the present invention. Preferably, the compositions are enriched in a polypeptide of the present invention. In the present context, the term "enriched" indicates that the glucoamylase activity of the composition has been increased, e.g., with an enrichment factor of 1.1.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus Aspergillus, preferably *Aspergillus aculeatus, Aspergillus awamori, Aspergillus niger,* or *Aspergillus oryzae,* or Trichoderma, Humicola, preferably *Humicola insolens,* or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having glucoamylase activity. The polypeptides may be used in the production of dextrose and fructose syrups (U.S. Pat. No. 3,912,590), beer with low carbohydrate content (Manners, *The Brewers Dogest,* December 1974, 56), alcohol from fermentation of raw starch (DE 3638529 C), according to established procedures in the art.

Signal Peptide

The present invention also relates to nucleic acid constructs comprising a gene encoding a protein operably linked to a nucleic acid sequence consisting of nucleotides 354 to 411 of SEQ ID NO:1 encoding a signal peptide consisting of amino acids 1 to 19 of SEQ ID NO:2, wherein the gene is foreign to the nucleic acid sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The nucleic acid sequence may be operably linked to foreign genes with other control sequences. Such other control sequences are described supra.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade.

Example 1

Detection of *Thielavia terrestris* glucoamylase

*Thielavia terrestris* NRRL 8126 was grown in 125 ml baffled shake flasks containing 25 ml of MY50 medium supplemented with 5% Nutriose at pH 4.2 for 3 days at 45° C. and 250 rpm. MY50 medium is composed per liter of 2 g of $MgSO_4.7H_2O$, 10 g of $KH_2PO_4$, 2 g of $K_2SO_4$, 5 g of CaCl$_2$.2H$_2$O, 2 g of citric acid, and 10 g of yeast extract. SDS-PAGE analysis of the culture broth supernatant using Novex 8–16% Tris-glycine SDS-PAGE gels according to manufacturer's suggested conditions (Novex, San Diego, Calif.) revealed a prominent protein band at 70 kDa.

N-terminal sequencing of the 70 kDa band was performed on an Applied Biosystems 476A Protein Sequencer (Perkin Elmer/Applied Biosystems Division, Foster City, Calif.) with on-line HPLC and liquid phase trifluoroacetic acid (TFA) delivery. The gel was electroblotted to a PVDF membrane (Novex, San Diego, Calif.) for 2 hours at 25 volts in 10 mM CAPS pH 11.0 buffer. The PVDF membrane was stained in 0.1% Commassie Blue R250 in 40% methanol/1% acetic acid and the 70 kDa band excised. The excised band was sequenced from a blot cartridge using sequencing reagents (Perkin Elmer/Applied Biosystems Division, Foster City, Calif.). Detection of phenylthiohydantoin-amino acids was accomplished by on-line HPLC using Buffer A containing 3.5% tetrahydrofuran in water with 18 ml of the Premix concentrate (Perkin Elmer/Applied Biosystems Division, Foster City, Calif.) containing acetic acid, sodium acetate, and sodium hexanesulfonate and Buffer B containing acetonitrile. Data was collected and analyzed on a Macintosh IIsi using Applied Biosystems 610 Data Analysis software (Perkin Elmer/Applied Biosystems Division, Foster City, Calif.). Sequence determinations were made by visualizing chromatograms against a light source.

The 70 kDa band was found to contain the N-terminus sequence SVDSFIATES (SEQ ID NO. 2). The sequence was homologous to the *Neurospora crassa* glucoamylase (Stone et al., 1993, *Curr. Genet.* 24: 205–211).

Example 2

Genomic DNA Isolation

*Thielavia terrestris* NRRL 8126 and *Neurospora crassa* 74-OR23-1A (Oak Ridge 74A, Fungal Genetics Stock Center, Kansas City, Kans.) were grown in 25 ml of 0.5% yeast extract-2% glucose (YEG) medium for 24 hours at 37° C. and 250 rpm. Mycelia were then collected by filtration through Miracloth™ (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg per ml and the mixture was then incubated at 37° C. for minutes. Proteinase K (200 μg/ml) was added and the tube was incubated an additional one hour at 37° C. Finally, the sample was centrifuged for 15 minutes at 12,000×g, and the supernatant was applied to a Qiaprep 8 manifold (QIAGEN Inc., Valencia, Calif.). The columns were washed twice with 1 ml of PB (QIAGEN Inc., Valencia, Calif.) and 1 ml of PE (QIAGEN Inc., Valencia, Calif.) under vacuum. The isolated DNA was eluted with 100 μl of TE, precipitated with ethanol, washed with 70% ethanol, dried under vacuum, resuspended in TE buffer, and stored at 4° C.

Example 3

Isolation of the *Neurospora crassa* glucoamylase Gene Probe

The oligonucleotide primers shown below were synthesized with an Applied Biosystems Model 294 DNA/RNA Synthesizer (Perkin Elmer/Applied Biosystems Division, Foster City, Calif.), according to the manufacturer's instructions, to PCR amplify *Neurospora crassa* glucoamylase gene fragments from genomic DNA. The forward oligonucleotide primer was designed to the 5' peptide sequence VDSYIQTE in the *Neurospora crassa* glucoamylase protein sequence. The reverse oligonucleotide primer was designed to the 3' peptide YNGNPWYL in the *Neurospora crassa* glucoamylase protein sequence.

Forward primer:
5'-GTCGACTCGTATATCCAGACCGAG-3' (SEQ ID NO. 3)

Reverse primer:
5'-GAGGTACCACGGGTTACCGTTGTA-3' (SEQ ID NO. 4)

Amplification reactions (100 μl) contained the following components: 1 μg *Neurospora crassa* genomic DNA (Example 2), 40 pmol forward primer, 40 pmol reverse primer, 200 μM each of dATP, dCTP, dGTP, and dTTP, 1×Taq polymerase buffer (Perkin-Elmer Corp., Branchburg, N.J.), and 2.5 Units of Taq polymerase (Perkin-Elmer Corp., Branchburg, N.J.). The reactions were incubated in a Perkin-Elmer Model 480 Thermal Cycler programmed as follows: Cycle 1 at 94° C. for 2 minutes, 45° C. for one minutes, and 72° C. for one minute; and cycles 2–30 each at 94° C. for one minute, 45° C. for one minute, and 72° C. for one minute.

The reaction products were isolated on a 1% agarose gel (Eastman Kodak, Rochester, N.Y.) using 4 mM Tris-20 mM sodium acetate-1 mM EDTA-Na$_2$ pH 7.2 (TAE) buffer. An approximately 800 bp product band was excised from the gel and purified using GenElute spin columns (Supelco, Bellefonte, PA) according to the manufacturer's instructions. The purified PCR product was subsequently cloned into a pCRII vector (Invitrogen, San Diego, Calif.) and the DNA sequence was determined using lac forward and reverse primers (New England BioLabs, Beverly, Mass.).

DNA sequencing of the 800 bp fragment showed that the amplified DNA fragment encoded a portion of the *Neurospora crassa* glucoamylase gene. The *Neurospora crassa* glucoamylase gene fragment was used to probe a *Thielavia terrestris* genomic DNA library. The 0.8 kb glucoamylase gene fragment was $^{32}$P-radiolabeled using the Random Primed DNA Labeling Kit (Boehringer Mannheim, Mannheim, Germany).

Example 4

Genomic DNA Library Construction

Genomic DNA libraries were constructed using the bacteriophage cloning vector λZipLox (Life Technologies, Gaithersburg, Md.) with *E. coli* Y1090ZL cells (Life Technologies, Gaithersburg, Md.) as a host for plating and purification of recombinant bacteriophage and *E. coli* DH10Bzip (Life Technologies, Gaithersburg, Md.) for excision of individual pZL1 clones containing the glucoamylase gene.

*Thielavia terrestris* genomic DNA was partially digested with Tsp509I and size-fractionated on 1% agarose gels using TAE buffer. DNA fragments migrating in the size range 3–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *Escherichia coli* Y1090ZL cells (Life Technologies, Gaithersburg, Md.). The unamplified genomic DNA library contained $3.1 \times 10^6$ pfu/ml (background titers with no DNA were $2.0 \times 10^4$ pfu/ml.

Example 5

Identification of *Thielavia terrestris* Glucoamylase Clones

Approximately 90,000 plaques from the library described in Example 5 were screened by plaque-hybridization using the 0.8 kb glucoamylase PCR fragment from *Neurospora crassa* (Example 4) as the probe. The DNA was cross-linked onto membranes (Hybond N+, Amersham, Arlington Heights, Ill.) using a UV Stratalinker (Stratagene, La Jolla, Calif.). The membranes were soaked for three hours at 45° C. in a hybridization solution containing 5×SSPE, 0.3% SDS, 50% formamide, and 10 µg/ml of denatured and sheared herring sperm DNA. The $^{32}$P-radiolabeled 0.2 kb glucoamylase gene fragment was denatured by adding sodium hydroxide to a final concentration of 0.1 M, and added to the hybridization solution at an activity of approximately $1 \times 10^6$ cpm per ml of hybridization solution. The mixture was incubated overnight at 45° C. in a shaking water bath. Following incubation, the membranes were washed once in 2×SSC with 0.2% SDS at 55° C. followed by two washes in 2×SSC at the same temperature. The membranes were dried on blotting paper for 15 minutes, wrapped in SaranWrap™, and exposed to X-ray film overnight at −70° C. with intensifying screens (Kodak, Rochester, N.Y.).

Based on the production of strong hybridization signals with the probe, 4 plaques were chosen for further study. The plaques were purified twice in *E. coli* Y1090ZL cells and the glucoamylase genes were subsequently excised from the λZipLox vector as pZL1-derivatives (D'Alessio et al., 1992, *Focus®* 14:76) using in vivo excision by infection of *E. coli* DH10BZL cells (Life Technologies, Gaithersburg, Md). The glucoamylase gene-containing colonies were inoculated into three ml of LB plus 50 µg/ml carbenicillin medium and grown overnight at 37° C. Miniprep DNA was prepared from each of these cultures using the Wizard 373 DNA Purification Kit (Promega, Madison, Wis.). One clone designated *E. coli* DH10BZI pEJG72 was shown by DNA sequencing to contain the full-length glucoamylase gene.

Example 6

DNA Sequence Analysis of *Thielavia terrestris* Glucoamylase Gene

DNA sequencing of the *Thielavia terrestris* glucoamylase gene contained in pEJG72 of *E. coli* DH10BZI was performed using Prism dye terminator chemistry on an ABI 377 DNA sequencer. A primer walking strategy was used to generate the nucleotide sequence of the gene.

The nucleotide sequence of the gene encoding the *Thielavia terrestris* glucoamylase and the deduced amino acid sequence thereof is shown in FIG. 1 (SEQ ID NOs. 1 and 2, respectively). Sequence analysis of the cloned gene revealed a coding sequence of 1890 bp (excluding the stop codon) encoding a protein of 630 amino acids sequence (SEQ ID NO. 2).

The coding sequence is punctuated by five introns which were determined based on the consensus rules for intronic features in filamentous fungi (Gurr et al., 1987, In J. R. Kinghorn (ed.), Gene Structure in Eukaryotic Microbes). The consensus for the 5' intron donor site appeared to be GTANGY (SEQ ID NO. 1) whereas the consensus for the 3' intron acceptor site appeared to be CAG (SEQ ID NO. 1). The position of intron I was exactly conserved with that seen in *N. crassa* and *Aspergillus nidulans* glucoamylase genes.

The palindrome 5'-GCGGGGCCCCGC-3' (SEQ ID NO. 1) found 194 bp upstream of the ATG site contained the CreA consensus binding sequence SYGGGG and shared almost perfect identity to a region 171 bp upstream of the ATG in the *Aspergillus nidulans* alcohol dehydrogenase I gene (alcA), which corresponds to one of the binding sites for the glucose-responsive repressor protein CreA (Kulmburg et al., 1993, *Mol. Microbiol.* 7: 847–857). In addition, the flanking of the palindrome by a direct and an inverted repeat of the sequence 5'-CCGCA-3' (SEQ ID NO. 1), the DNA-binding motif for a positive regulatory protein (ALCR) required for the activation of the alc genes in *Aspergillus nidulans* (Kulmburg et al., 1992, *Mol. Cell. Biol.* 12: 1932–1939), might suggest a "direct competition" type *Thielavia terrestris* glucoamylase regulation mode similar to that of ALCR in *Aspergillus nidulans* (Mathieu and Felenbok, 1994, *EMBO J.* 13: 4022–4027). Similar regulation structure has also been reported for the *Thielavia heterothallica* cellobiose dehydrogenase (Boominathan et al., 1996, *Abstracts of the General Meeting of the American Society for Microbiology* 96: 531).

The exons of the glucoamylase gene appeared to be more GC-rich than introns (66% compared to 57%). The codon usage suggested a marked codon bias from *Thielavia terrestris* for codons ending in C. For the four codon families, the codon ending in G was preferred over that ending in T when C was not used. For the two codon families not using C, the codon ending in G was preferred. The use of codons ending in A was minimal. A palindrome 5'-GCGGGGCCCCGC-3' (SEQ ID NO:1), which was 194 bp upstream of the ATG site, was flanked by a direct and an inverted repeat of the sequence CCGCA.

The predicted mature glucoamylase polypeptide has a molecular mass of 49.4 kdal and an isoelectric point of 4.76. Based on the rules of van Heijne (van Heijne, 1984, *Journal of Molecular Biology* 173: 243–251), the first 19 amino acids likely comprise a secretory signal peptide which directs the nascent polypeptide into the endoplasmic reticulum.

A starch-binding domain (Gln540-Gln630) and a catalytic domain (Gla18-Ala491) were detected in the *Thielavia terrestris* glucoamylase. The former was found linked to the C-terminus of the latter by a linker (Thr492-Thr539) rich in glycosylated threonines. The structure of *Thielavia terrestris* glucoamylase's catalytic domain suggests that it belongs to the subfamily 15 of glucoamylases (Coutinho and Reilly, 1997, *Proteins: Struct. Funct. Genet.* 29: 334–347).

A comparative multiple alignment of glucoamylase polypeptide sequences was determined by the ClustalW method (Higgins, 1989, *CABIOS* 5: 151–153; Thompson et al., 1994, *Nucleic Acids Research* 22: 4673–4680; Thompson et al., 1997, *Nucleic Acids Research* 25: 4876–4882) using the LASERGENE™ MEGALIGN™ software (DNASTAR, Inc., Madison, Wis.) with a blosum weight matrix and gap extension penalty of 0.03 to 0.05 and the following multiple alignment parameters: Gap penalty of 10 and gap length penalty of 10. Pairwise alignment parameters were Ktuple=1, gap penalty=3, windows=5, and diagonals=5. The comparative alignment showed that the deduced amino acid sequence of the *Thielavia terrestris* glucoamylase shares 64.5% identity with a glucoamylase from *Neurospora crassa* (SwissProt Acc. No. P14804).

Plasmid pEJG72 was cloned using Stratagene's Epicurian Coli XL1Blue competent cells (Stratagene, La Jolla, Calif.) according to the manufacturer's instructions and one clone designated *E. coli* pEJG72/XL1Blue was deposited on Oct. 27, 2000, with the Agricultural Research Service Patent Culture Collection, Northern Regional Research Center, 1815 University Street, Peoria, Ill., 61604, and assigned the accession number NRRL B-30358.

Example 7

Construction of a *Thielavia terrestris* Glucoamylase Expression Vector

The full-length *Thielavia terrestris* glucoamylase coding sequence was amplified by PCR from pEJG72 (Example 5) using the following primers, which were synthesized with an Applied Biosystems Model 294 DNA/RNA Synthesizer, to incorporate a 5' ATG and a 3' PacI site.
5'-atgATGCGCCGTCTTCAGCTCTTG-3' (SEQ ID NO:5)
5'-gggttaattaaTTACTGCCAGGTATC-3' (SEQ ID NO:6)
(the capital letters correspond to the sequence present in the glucoamylase gene)

Amplification reactions (50 µl) contained the following components: 0.2 µg of pEJG72, 50 pmol of each primer, 10 mM blend of dATP, dCTP, dGTP, and dTTP, 5 units of Amplitaq (Perkin Elmer), and 5% DMSO in 1×Amplitaq Buffer. The reactions were incubated in a Perkin Elmer 9600 thermocycler programmed for one cycle at 94° C. for 1 minute, 45° C. for 15 seconds, and 72° C. for 15 seconds; 25 cycles each at 94° C. for 15 seconds, 45° C. for 15 seconds, and 72° C. for 15 seconds; and one final cycle at 94° C. for 15 seconds, 50° C. for 15 seconds, and 72° C. for 6 minutes.

The reaction products were isolated on a 0.8% agarose gel using TAE buffer where a 2.2 kb product band was excised from the gel and purified using a QIAquick kit (QIAGEN Inc., Chatsworth, Calif.) according to the manufacturer's instructions. The 2.2 kb fragment was cloned into pCR®2.1-TOPO (Invitrogen, San Diego, Calif.) after addition of 3' A-overhangs according to the manufacturer's suggested protocol.

Figure 3:
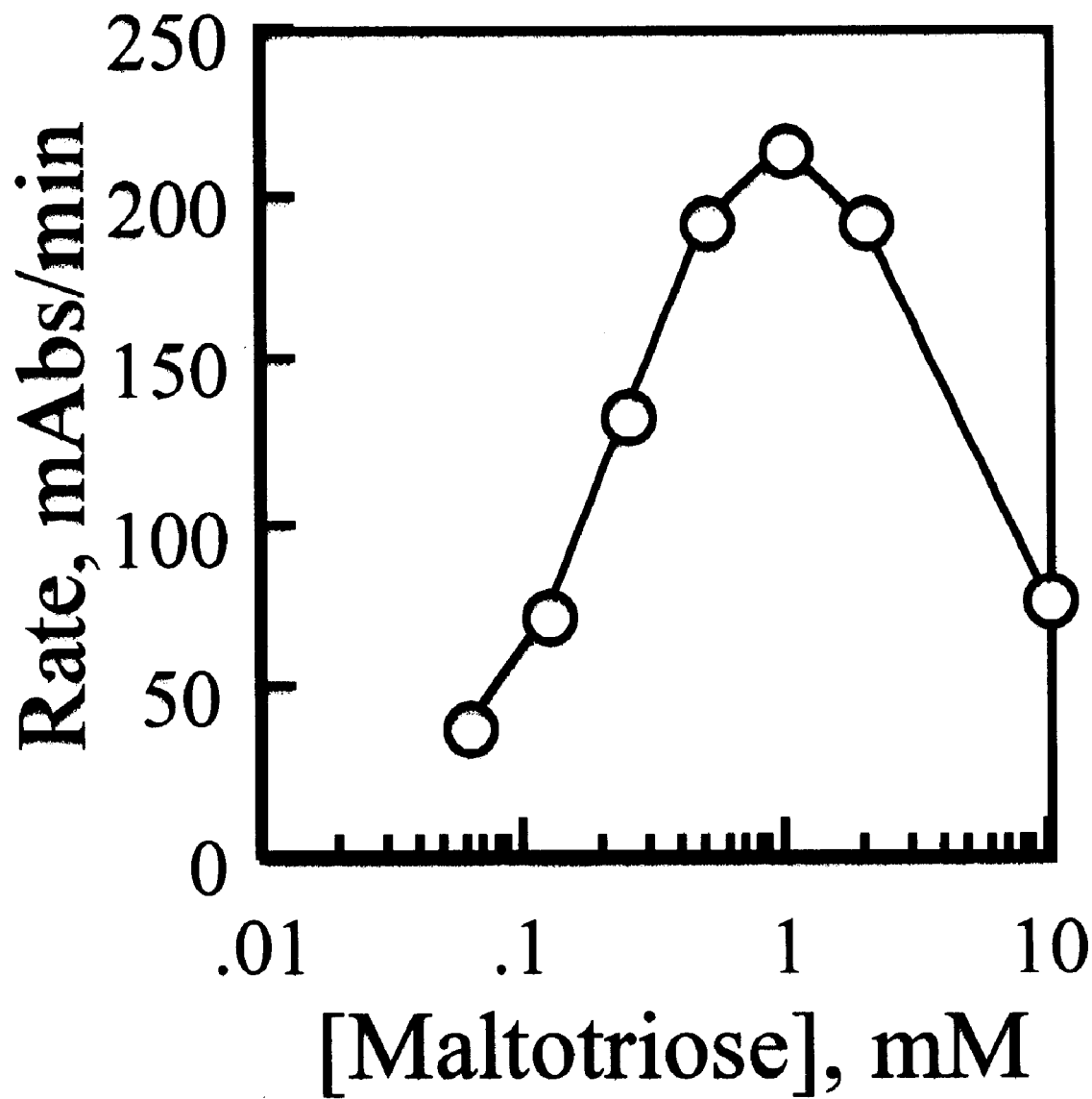
FIG. 3 shows the dependence of *Thielavia terrestris* ATCC 20627 glucoamylase activity on substrate concentration at pH 4.

The insert from one selected clone was removed by digestion with SwaI and PacI, gel purified, and ligated into similarly digested pBANe15 (FIG. 2) to yield pEJG20 (FIG. 3). pEJG20 contains an *Aspergillus oryzae* α-amylase promoter, an *Aspergillus niger* glucoamylase terminator, and the *Aspergillus nidulans* amdS selectable marker.

Example 8

Expression of *Thielavia terrestris* Glucoamylase Gene in *Aspergillus oryzae* pEJG20 was introduced into an *Aspergillus oryzae* host JaL228 using the following protoplast transformation method. The transformation was conducted with protoplasts at a concentration of ca. $2 \times 10^7$ protoplasts per ml. One hundred µl of protoplasts were placed on ice with ca. 5 µg of pEJG20; 250 µl of 60% PEG 4000, 10 mM Tris-HCl, pH 7.5, 10 mM $CaCl_2$ was added, and the protoplasts were incubated at 37° C. for 30 minutes. Three mls of STC (1.2 M sorbitol, 10 mM Tris-HCl, pH 7.5, and 10 mM $CaCl_2$) was added. The solution was mixed gently and poured onto COVE transformation plates. The COVE transformation plates were composed per liter of 0.52 g of KCl, 0.52 g of $MgSO_4$-$7H_2O$, 1.52 g of $KH_2PO_4$, 1 ml of trace metals described below, 342.3 g of sucrose, 25 g of Noble agar, 10 ml of 1 M acetamide, 10 ml of 3 M CsCl). The trace metals solution (1000×) was composed per liter of 22 g of $ZnSO_4$-$7H_2O$, 11 g of $H_3BO_3$, 5 g of $MnCl_2$-$4H_2O$, 5 g of $FeSO_4$-$7H_2O$, 1.6 g of $(NH_4)_6Mo_7O_{24}$, and 50 g of $Na_4EDTA$. Plates were incubated 7 days at 37° C. Transformants were transferred to plates of the same medium and incubated 2 days at 37° C. Totally, 29 transformants were recovered by their ability to grow on COVE medium using acetamide as sole nitrogen source.

Each transformant was transferred to a COVE plate. From the plates, spores from each transformant were inoculated into 1 ml of minimal medium in 24-well plates and grown at 34° C., 150 rpm. The minimal medium was composed per liter of 6 g of $NaNO_3$, 0.52 g of KCl, 1.52 g of $KH_2PO_4$, 1 ml of trace metals solution, 1 g of glucose, 500 mg of $MgSO_4$-$7H_2O$, 342.3 g sucrose and 20 g of Noble agar per liter (pH 6.5). The trace metals solution (1000×) was composed per liter of 22 g of $ZnSO_4$-$7H_2O$, 11 g of $H_3BO_3$, 5 g of $MnCl_2$-$4H_2O$, 5 g of $FeSO_4$-$7H_2O$, 1.6 g of $CoCl_2$-$5H_2O$, 1.6 g of $(NH_4)_6Mo_7O_{24}$, and 50 g of $Na_4EDTA$. Negative controls included the untransformed host and a glucoamylase-deficient *Aspergillus oryzae* strain. Aliquots of 50 µl of the culture media were removed at 4, 6, and 8 days for glucoamylase activity assay using p-nitrophenyl-glucoside as the substrate as described below. Untransformed *Aspergillus oryzae* JaL228 was grown and tested to check the background glucoamylase activity caused by the native *Aspergillus oryzae* glucoamylase.

Glucoamylase activity was measured by incubating 50 µl of each supernatant with 100 µl of 50 mM sodium acetate pH 4.3 containing 1 mg/ml p-nitrophenyl-glucoside and 150 µl of 1 M Tris pH 8 at 37° C. for 30 minutes. Activity was monitored photometrically at 405 nm using a Thermomax microplate reader (Molecular Devices, Sunnyvale, Calif. in 96-well micro-plates (Costar, Coming, N.Y., serocluster grade).

The results for the highest producers are shown in Table 1. The highest glucoamylase activity of the transformants was 5 and 3 times that of the untransformed host at 6 and 8 days, respectively.

Since the untransformed *Aspergillus oryzae* host produced a native glucoamylase, the presence of the *Thielavia terrestris* glucoamylase gene in the transformants was analyzed by PCR amplification using the same procedure described in Example 3 and the following glucoamylase-specific primers:

5'-ATGATGCGCCGTCTTCAGCTCTTG-3' (SEQ ID NO:7)
5'-GGGATGCATTTACTGCCAGGTATC-3' (SEQ ID NO:8)

PCR amplification revealed that 28 of 29 transformants possessed a 2.2 kb glucoamylase gene band.

TABLE 1

Expression of *Thielavia terrestris* glucoamylase in 24-well plate

|  | Day 4 | Day 6 | Day 8 |
|---|---|---|---|
| Nutient media only | 0.064 | 0.064 | 0.068 |
| glucoamylase-*A. oryzae*\* | 0.084 | 0.060 | 0.084 |
| Untransformed host | 0.080 | 0.059 | 0.259 |
| Transformant #6 | 0.177 | 0.278 | 0.724 |
| Transformant #10 | 0.127 | 0.161 | 0.558 |
| Transformant #11 | 0.172 | 0.172 | 0.530 |
| Transformant #14 | 0.186 | 0.186 | 0.086 |
| Transformant #21 | 0.095 | 0.095 | 0.156 |
| Transformant #23 | 0.092 | 0.105 | 0.185 |
| Transformant #24 | 0.137 | 0.137 | 0.330 |
| Transformant #29 | 0.118 | 0.078 | 0.250 |

*A untransformed *Aspergillus oryzae* strain deficient *Aspergillus oryzae* glucoamylase.

Transformant #6 was then grown in a 2-liter fermentor using a fed-batch mode with maltodextrin, urea, and yeast extract at pH 7 and 34° C. for 188 hours. The broth was used as a source for purifying and characterizing the recombinant glucoamylase.

Example 9

Purification of Recombinant *Thielavia terrestris* Glucoamylase

The recombinant glucoamylase described in Example 8 was purified using a combination of ultrafiltration, anion-exchange, cation-exchange, and hydrophobic interaction chromatography. Chromatography was carried out in a Pharmacia's FPLC (Pharmacia Biotech AB, Uppsala, Sweden) and electrophoresis was made with a Bio-Rad's minicell apparatus and ready gels (BioRad Laboratories, Hercules, Calif.). The cell-free broth (pH 7.1, 13 mS conductivity) was filtered with Whatman #2 paper and subjected to ultrafiltration using an Amicon Spiral-Concentrator (S1Y10 membrane cartridge). The concentrate was washed with distilled water to 1 mS conductivity using a spiral concentrator.

Fractions were assayed for glucoamylase activity using a glucose oxidase kit (Sigma Chemical Co., St. Lousi, Mo.) according to the manufacturer's instructions with 0.1 M maltotriose as substrate.

The washed, concentrated broth (pH 7.1, 1 mS) was then loaded onto a Q-Sepharose column (Pharmacia Biotech AB, Uppsala, Sweden, XK26, 180 ml of gel, pre-equilibrated with 10 mM Tris-HCl pH 7.5). The active fraction, which eluted from the column during loading/washing, was applied to an SP-Sepharose column (Pharmacia Biotech AB, Uppsala, Sweden, XK-16, 60 ml gel, pre-equilibrated with 10 mM Tris-HCl pH 7.5). Like the Q-Sepharose run, most of the glucoamylase activity passed through the column during loading/washing.

Ammonium sulfate was added to the fraction to a final concentration of 1.7 M and loaded onto a Phenyl Sepharose column (Pharmacia Biotech AB, Uppsala, Sweden, XK 26, 180 ml, pre-equilibrated with 50 mM sodium phosphate pH 7, 1.7 M ammonium sulfate. The glucoamylase was eluted by a linear gradient (5 bed-volume) of 50 mM sodium phosphate, pH 7. Fractions containing glucoamylase activity were subjected to a dialysis against 10 mM sodium phosphate pH 7 (final ammonium sulfate concentration was less than 0.25 mM).

SDS-PAGE analysis of the purified recombinant *Thielavia terrestris* glucoamylase using a Novex 8–16 gradient gel showed a single band of 75 kDa, a molecular weight higher than the predicted 62 kDa from the DNA sequence, which is likely due to glycosylation. N-terminal sequencing of the recombinant enzyme, performed as described in Example 1, was identical to the wild type enzyme, indicating correct processing by the *Aspergillus oryzae* host. Overall a recovery yield of 44% and an 89-fold purification (based on activity/$Abs_{280}$) were obtained.

Example 10

Characterization of Recombinant *Thielavia terrestris* Glucoamylase

Characterization of the recombinant *Thielavia terrestris* was performed. The spectral data were recorded on a Shimadzu UV160U spectrophotometer (Shimadzu, Pleasanton, Calif.) with 1-cm quartz cuvette. Glucoamylase activity was measured using the assay method described below.

The glucose-releasing activity of glucoamylase (on maltooligosaccharide) was measured using a glucose oxidase assay kit (Sigma Chemical Co., St. Louis, Mo.) according to the manufacturer's instructions. The method showed a linear correspondence of the absorbance change (ΔAbs) to [glucose] at 28–389 M glucose range (rate=0.30×[glucose]−1.01), where the units were: rate, 0.001 Abs/minutes (at 490 nm with 0.31 cm path-length) for the rate and $\mu$M for [glucose]). To obtain the correct glucoamylase activity, glucoamylase samples were subjected to ultrafiltration and the resulting retentate (glucoamylase enriched) and filtrate (containing no glucoamylase) were assayed by the glucose oxidase kit. The background substrate oxidation was then subtracted from the data obtained for the glucoamylase samples. Another glucoamylase activity assay comprised of glucoamylase hydrolysis on maltose and glucose detection by a Glucose GOD-Perid kit (Boehringer Mannheim, Indianapolis, Ind.) according to the manufacturer's instructions. In this assay, 900 l of 50 mM sodium acetate, pH 4.3, containing 1% maltose, pre-incubated for 5 minutes at 37° C., was mixed with 20 $\mu$l of glucoamylase solution in 50 mM sodium acetate pH 4.3. After a 10 minute incubation, 80 $\mu$l of 1 M NaOH was added to inactivate glucoamylase and the mixture was chilled on ice to prevent the non-enzymatic, basic hydrolysis of maltose. A 20 $\mu$l volume of the solution was then mixed with 200 $\mu$l of GOD-Perid solution. After a 30 minute incubation at room temperature, the absorbance at 650 nm was measured. The Prism program (from GraphPad, San Diego, Calif.) was used to calculate $K_m$ and $V_{max}$ by non-linear regression. The parameter $k_{cat}$ (mole glucose produced per mole glucoamylase per min) was calculated by $k_{cat}=\{(V_{max}+1.01)/0.30\}/[\text{enzyme}]$, where the units were 0.001 Abs /minute for $V_{max}$ and $\mu$M for [enzyme]. The 124 mM$^{-1}$ cm$^{-1}$ value, calculated from the amount of tyrosine, phenylalanine, and cysteine as deduced from the DNA sequence, was used for the extinction coefficient of *Thielavia terrestris* glucoamylase at 280 nm.

pH-activity Profile

The pH-activity profile was determined as follows: 10 $\mu$l of *Thielavia terrestris* glucoamylase (0.11 mg/ml), 10 $\mu$l of 3 M maltotriose stock, and 5 $\mu$l Britton and Robinson buffer (pH ranging from 3 to 11) were preincubated (in duplicate) for 3 minutes. Then 50 $\mu$l of Sigma's GO glucose oxidase assay reagent and 25 $\mu$l of H$_2$O were added and the absorption change was monitored at 490 nm. The concentration of maltotriose stock varied from 0.63 to 100 mM to ensure that the rate reading covered the initial (linear) phase to the (substrate-) saturating phase.

Figure 5:
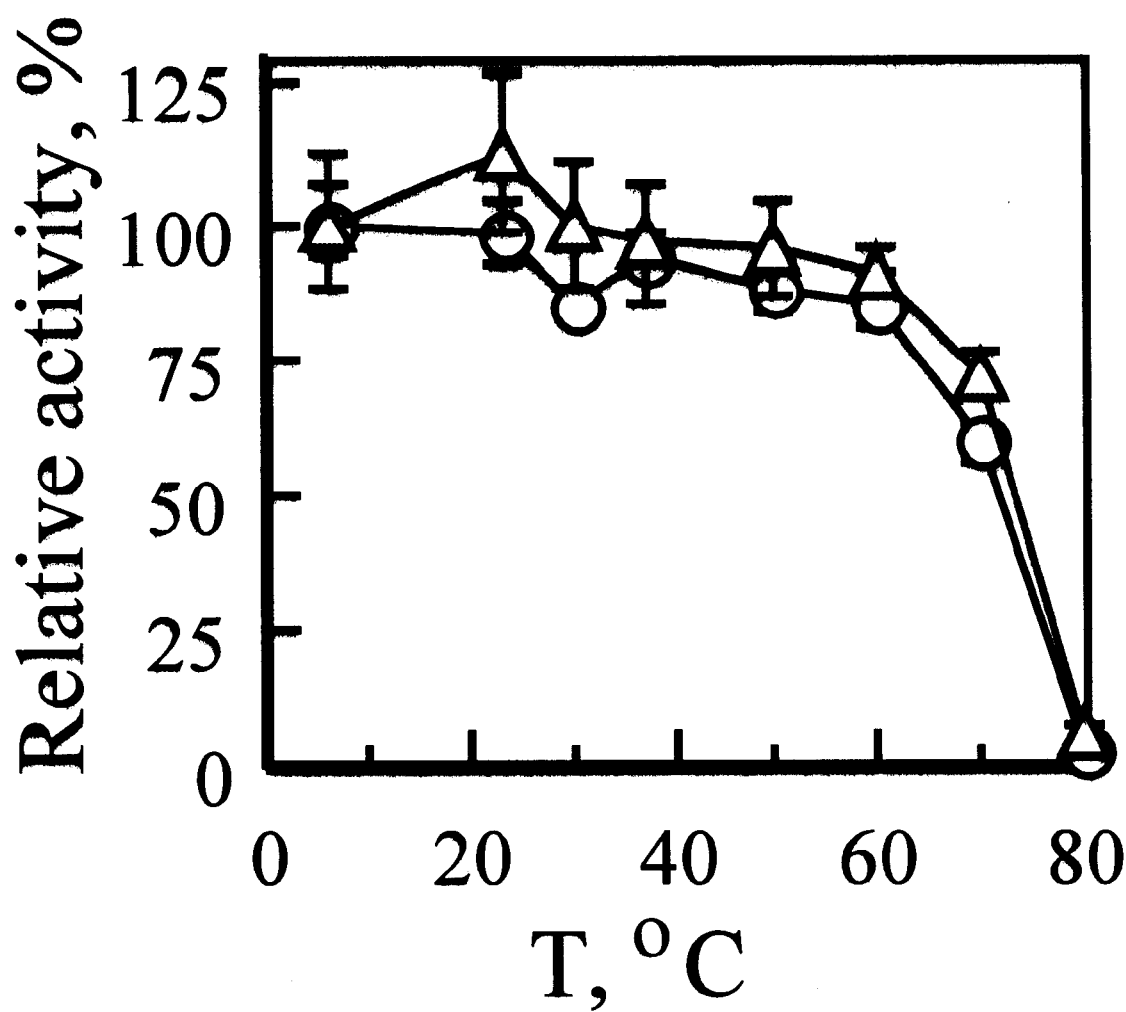
FIG. 5 shows the thermostability of a *Thielavia terrestris* ATCC 20627 glucoamylase.

The pH optimum for the *Thielavia terrestris* glucoamylase was 4.0 as shown in FIG. 5. The pH optimum was similar to the pH optima for other glucoamylase: 3.5–5.0 for *Aspergillus niger* glucoamylase (Ono et al., 1988, *Agric. Biol. Chem.* 52: 1699–1706), 4 for *Aspergillus awamori* glucoamylase (Sierks and Svensson, 1993, *Biochemistry* 32: 1113–1117), 4.5 for Aspergillus spp K-27 glucoamylase (Abe et al., 1990, *Carbohydrate Res.* 203: 129–138), and 4 for *Hormoconis resinae* glucoamylase (Fagerström et al., 1990, *J. Gen. Microbiol.* 136: 913–920). However, the pH optimum was more acidic than the pH optimum of 5 for *Aspergillus hennebergi* glucoamylase (Alazard and Baldensperger, 1982, *Carbohydrate Res.* 107: 231–241), 5.5 for *Trichoderma reesei* glucoamylase (Fagerström and Kalkkinen, 1995, *Biotechnol. Appl. Biochem.* 21: 223–231), 6 of *Humicola grisea* glucoamylase (Campos and Felix, 1995, *Appl Environ. Microbiol.* 61: 2436–2438), and 5–6 of *Chalara paradoxa* glucoamylase (Monma et al., 1987, *Carbohydrate Res.* 159: 255–261).

Temperature-activity Profile

The temperature-activity profile was measured in quadruplicate at 4, 22, 30, 37, 50, 60, 70, and 80° C. First, 100 μl of 10 mM maltotriose stock, 50 μl of Britton and Robinson pH 4 buffer, and 95 μl of H$_2$O were mixed and pre-incubated at the selected temperature. After 30 minutes, 5 μl *Thielavia terrestris* glucoamylase stock (0.11 mg/ml) was added and the solution was kept at the same temperature. After 20 minutes, the solutions were chilled (in ice-water) and briefly centrifuged (in 0.7-ml microcentrifuge tubes). Then 25 μl of these solutions were subjected to the glucoamylase assay by mixing with 50 μl of glucose oxidase reagent and 25 μl of H$_2$O as described above.

At pH 4 with maltotriose as the substrate, *Thielavia terrestris* glucoamylase showed a temperature optimum in the range of 60–70° C. (FIG. 8), which was comparable to the temperature optimum of 70° C. for *Aspergillus hennebergi* glucoamylase (Alazard and Baldensperger, 1982, *Carbohydrate Res.* 107: 231–241), 60–65° C. for *Aspergillus niger* glucoamylase (Ono et al., 1988, *Agric. Biol. Chem.* 52: 1699–1706), 60° C. for *H. grisea* glucoamylase (Campos and Felix, 1995, *Appl. Environ. Microbiol.* 61: 2436–2438), and 70° C. for *T reesei* glucoamylase (Fagerström. and Kalkkinen, 1995, *Biotechnol. Appl. Biochem.* 21: 223–231); but higher than the temperature optimum of 55–60° C. for *H. resinae* glucoamylase (Fagerström et al., 1990, *J. Gen. Microbiol.* 136: 913–920) and 50° C. for *C. paradoxa* glucoamylase (Monma et al., 1987, *Carbohydrate Res.* 159: 255–261).

Thermostability

The thermostability of the *Thielavia terrestris* glucoamylase was determined by incubating a solution 10 μl of the glucoamylase (0.11 mg/ml) and 5 μl of Britton and Robinson pH 4 buffer (in quadruplicate) at 4, 22, 30, 37, 50, 60, 70, and 80° C., respectively, for 30 minutes. The solutions were then chilled (in ice-water) and briefly centrifuged (in 0.7-ml micro-centrifuge tubes) before being transferred to a 96-well microplate for glucoamylase activity assay. One assay was made by adding simultaneously 10 μl of 10 mM maltotriose, 50 μl of glucose oxidase assay reagent, and 25 μl of H$_2$O to the *Thielavia terrestris* glucoamylase solution to start the reaction, whereas another assay was made by pre-incubating the *Thielavia terrestris* glucoamylase solution with the maltotriose stock for 3 minutes before adding the glucose oxidase assay reagent and H$_2$O.

Figure 6:
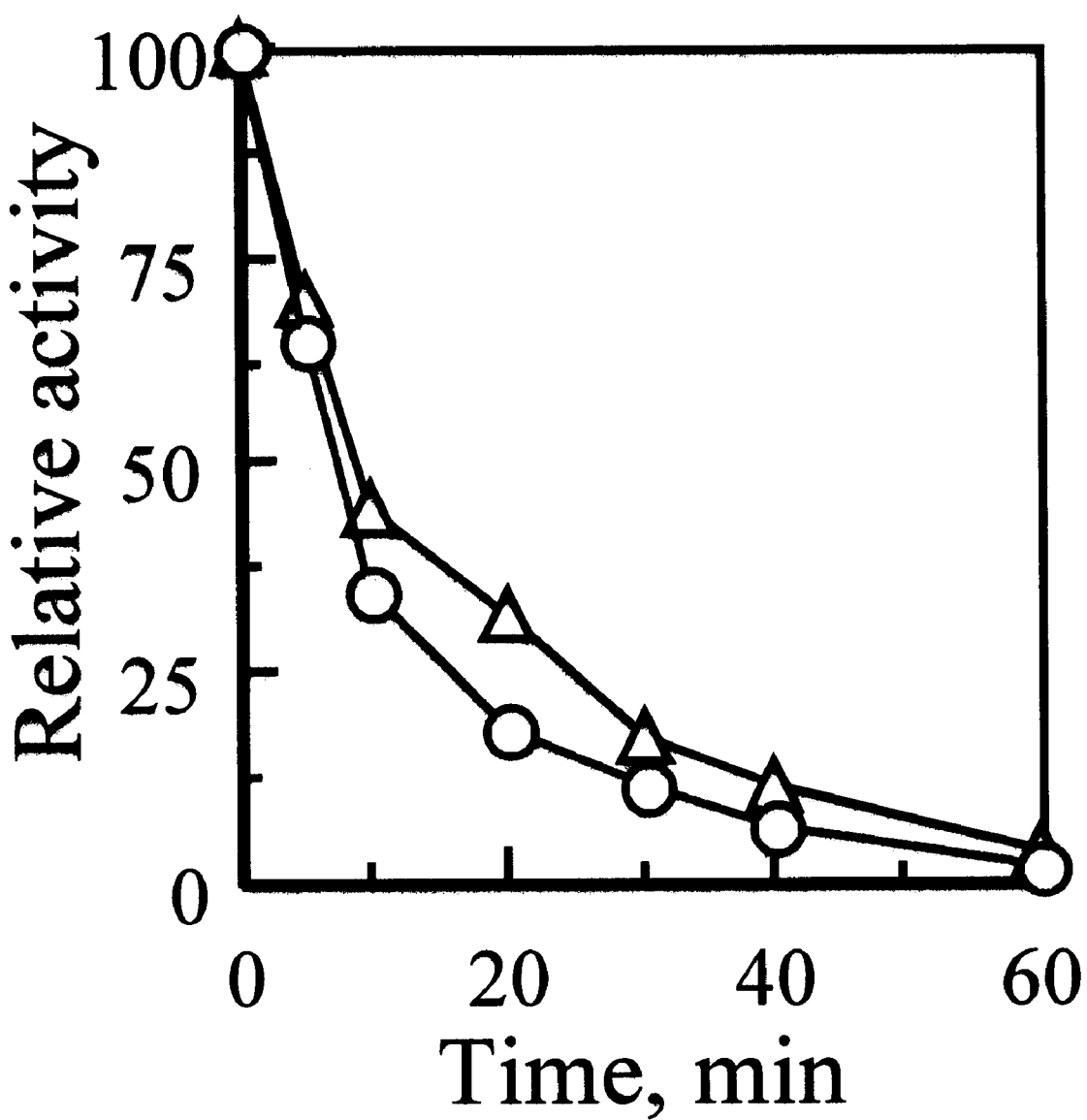
FIG. 6 shows the thermal stability of *Thielavia terrestris* ATCC 20627 glucoamylase and *Aspergillus niger* glucoamylase at 70° C. Enzyme tested: (o) *Aspergillus niger* glucoamylase, (Δ) *Thielavia terrestris* ATCC 20627 glucoamylase. Buffer used: 50 mM sodium acetate, pH 4.3.

The results as shown in FIG. 6 demonstrated that the *Thielavia terrestris* glucoamylase was stable at temperatures as high as 60° C. At 70° C., the glucoamylase retained 60–70% of its original activity after 30 minute incubation.

The *Thielavia terrestris* glucoamylase retained 60% of its activity after being incubated at pH 4 and 70° C. for 30 minutes. This thermostability was comparable to that of *Aspergillus terreus* glucoamylase (Ghose et al., 1990, *FEMS Microbiol. Lett.* 66: 345–350) but higher than the glucoamylase from *Aspergillus hennebergi* (Alazard and Baldensperger, 1982, *Carbohydrate Res.* 107: 231–241), *Aspergillus niger* (Ono et al., 1988, *Agric. Biol. Chem.* 52: 1699–1706), Aspergillus spp K-27 (Abe et al., 1990, *Carbohydrate Res.* 203: 129–138), *Aspergillus awamori* (Libby et al., 1994, *Prot. Engineer.* 7: 1109–1114), *H. resinae* (Fagerström et al., 1990, *J. Gen. Microbiol.* 136: 913–920), *T. reesei* (Fagerström et al., 1995, *Biotechnol. Appl. Biochem.* 21: 223–231), *H. grisea* (Campos et al., 1995, *Appl. Environ. Microbiol.* 61: 2436–2438), and *C. paradoxa* (Monma et al., 1987, *Carbohydrate Res.* 159: 255–261).

Figure 7A:
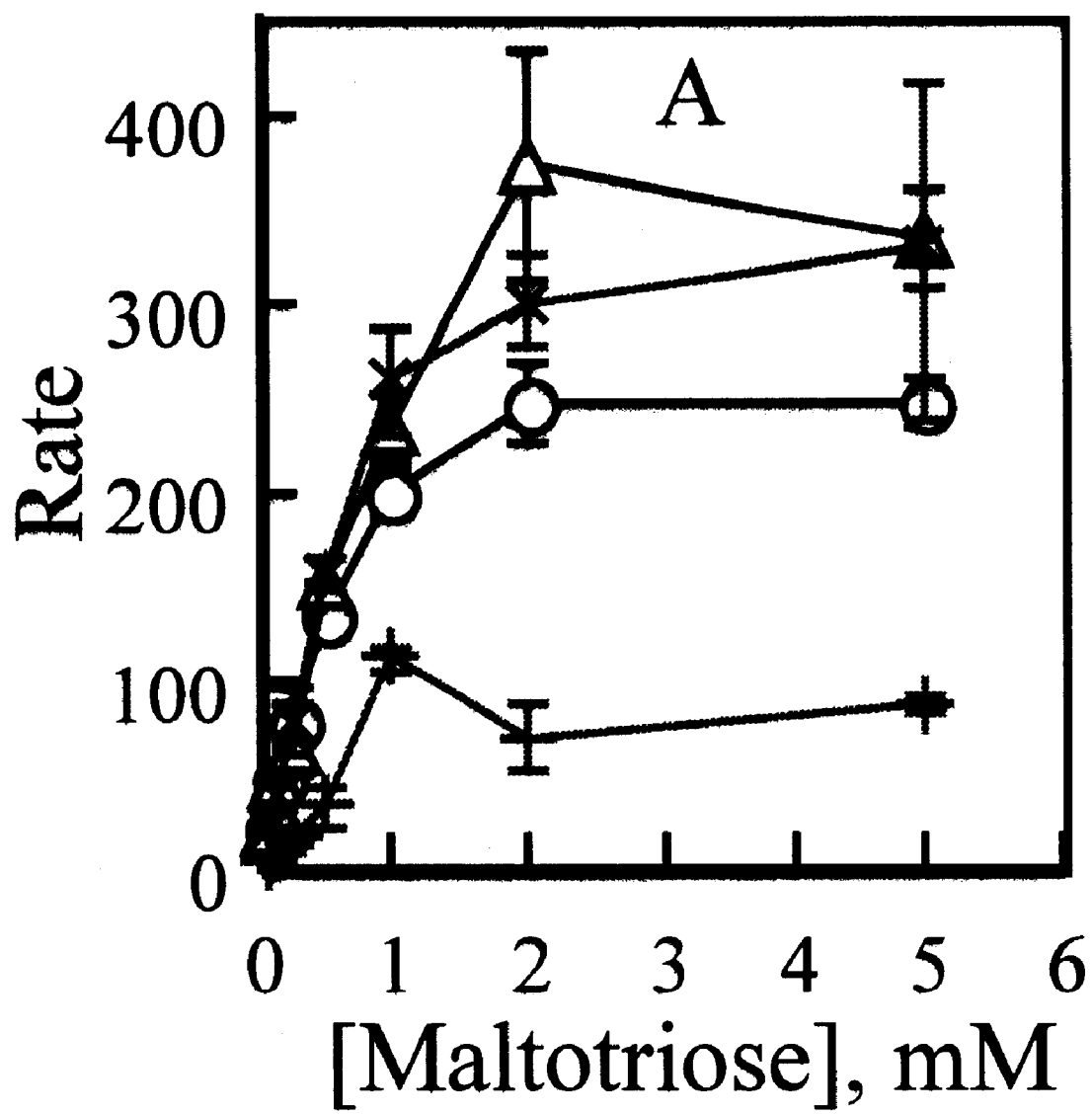
FIGS. 7A and B show the thermal activity of *Thielavia terrestris* ATCC 20627 glucoamylase. (A) Rate profiles at 50° C. (o), 60° C. (Δ), 70° C. (×), and 80° C. (+). (B) Relative activity for 0.25 (o) and 0.5 mM (Δ) maltotriose. The concentration of *Thielavia terrestris* glucoamylase was 1.1 μg/ml.
Figure 7B:
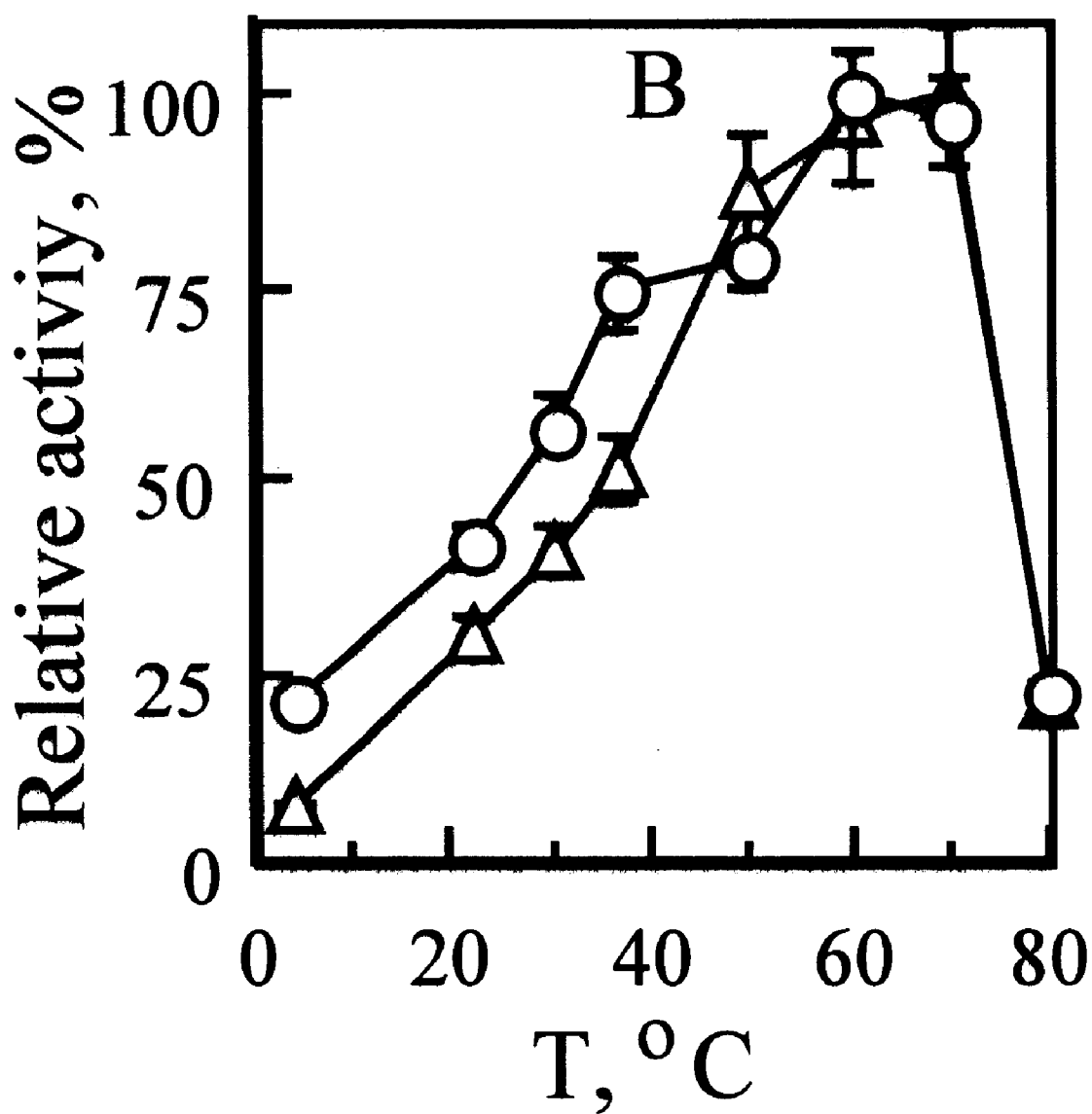

The thermal stability of *Thielavia terrestris* glucoamylase was compared to an *Aspergillus niger* glucoamylase (AMG™, available from Novo Nordisk A/S, Bagsvaerd, Denmark) at 70° C. and pH 4.3. Specifically, 950 μl of 50 mM sodium acetate pH 4.3, pre-incubated for at least 5 minutes at 70° C., was mixed with 50 μl of 1–2 mg of each glucoamylase per ml. After incubating at 70° C. for 0, 5, 20, 30, 40, and 60 minutes, 40 μl aliquots of the solutions were removed in duplicate, chilled on ice, and assayed for glucoamylase activity using a Boehringer Mannheim GOD-Perid kit according to the manufacturer's instructions. FIG. 7 shows the slightly superior thermal stability of *Thielavia terrestris* glucoamylase at 70° C. in comparison with the *Aspergillus niger* glucoamylase.

To measure the thermal transition by differential scanning calorimetry, 500 μl of *Thielavia terrestris* glucoamylase (with an Abs$_{280}$ of 8.6 in 50 mM sodium acetate pH 4.5) was scanned from 20 to 110° C. at a rate of 90° C. per hour using a VP-DSC instrument (MicroCal, Inc., Northampton, Mass.). The thermogram showed a transition around 71° C. for the *Thielavia terrestris* glucoamylase. The T$_d$ was estimated to be between 69 and 72° C. because of the precipitation of the glucoamylase (exothermic transition following the endothermic transition derived from the thermal unfolding of *Thielavia terrestris* glucoamylase).

Catalytic Constants

The *Thielavia terrestris* glucoamylase at 11 μg/ml or 0.18 μM showed a K$_m$ of 0.33±0.07 mM and a k$_{cat}$ of (5.5±0.5)× 10$^3$ min$^{-1}$ for maltotriose hydrolysis at pH 4. At 37° C. and pH 4.3, the *Thielavia terrestris* glucoamylase showed a specific activity almost 2-fold higher than that of the *Aspergillus niger* glucoamylase in hydrolyzing maltose.

Figure 4A:
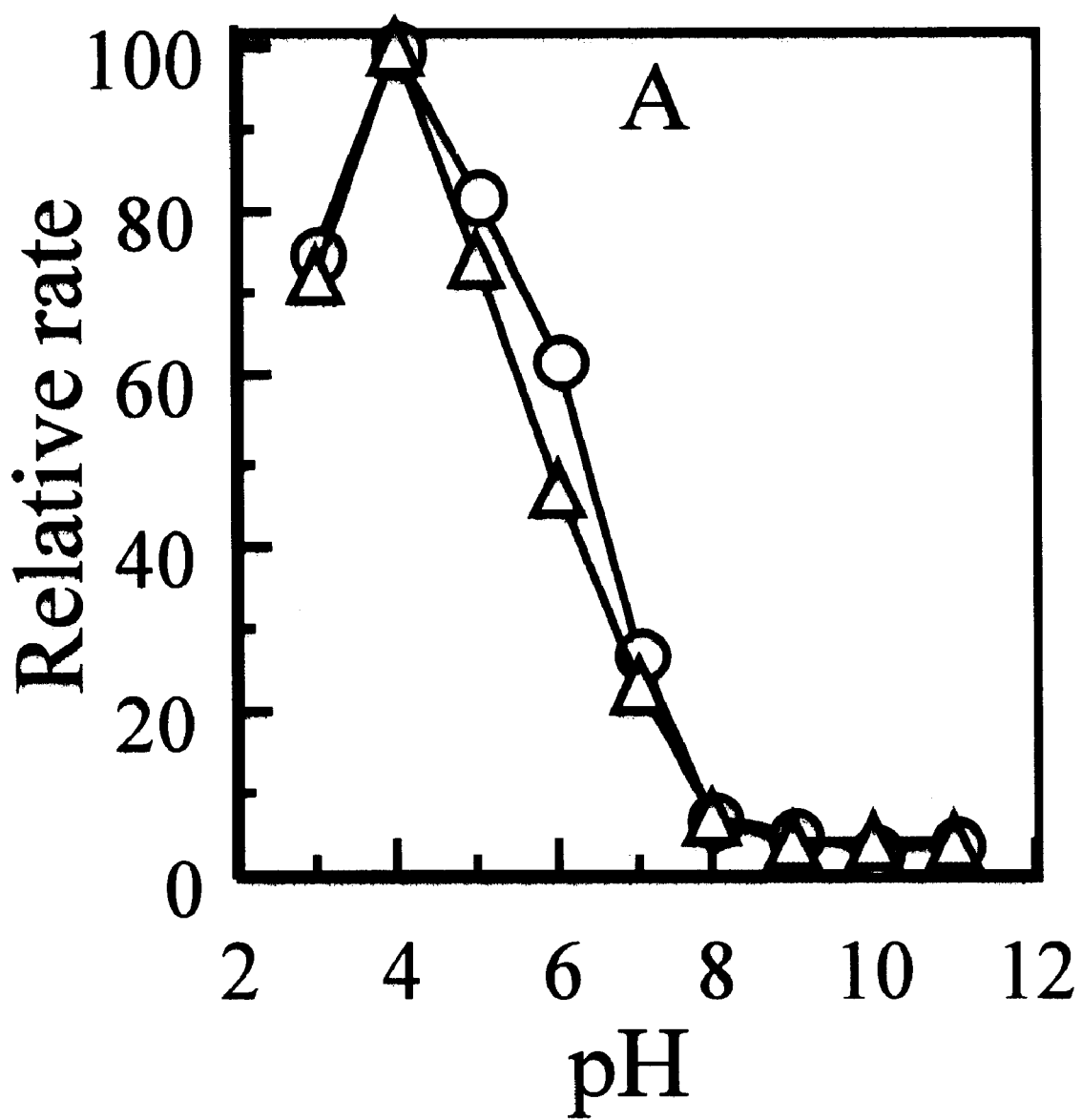
FIGS. 4A, B, and C show the dependence of *Thielavia terrestris* ATCC 20627 glucoamylase activity on pH. (A) For initial rate. Initial [maltotriose]: (O), 0.25 mM; (Δ), 0.50 mM. (B) For $K_m$ (O) and $k_{cat}$ (Δ). (C) For $\log(k_{cat}/K_m)$. $k_{cat}/K_m$ unit: $M^{-1}min^{-1}$.
Figure 4B:
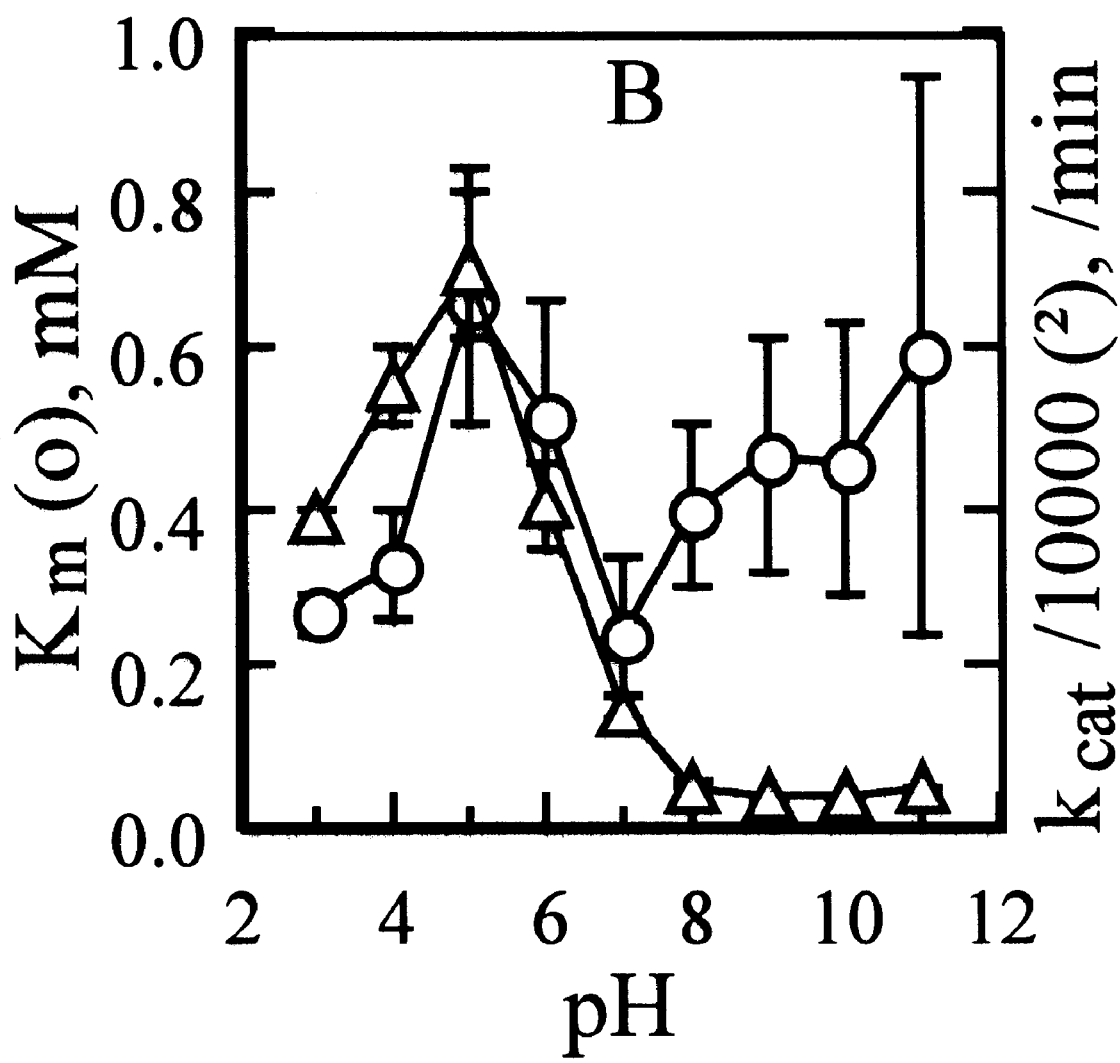
Figure 4C:
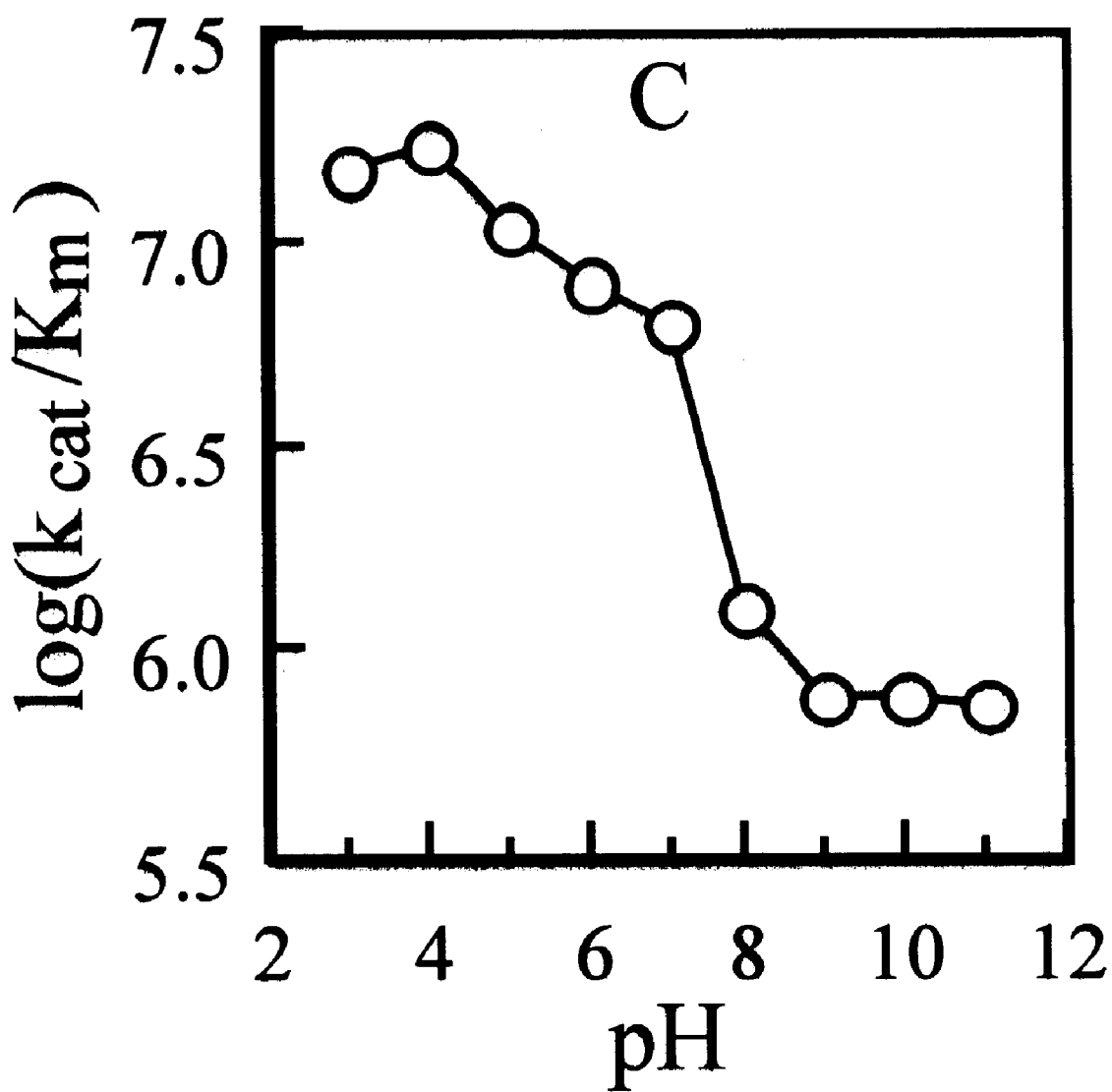

At pH 3–7, the glucose oxidase assay yielded initial rates dependent on maltotriose concentration. The rate exhibited a Michaelis pattern when the maltotriose concentration was =2 mM. Above 2 mM, a reduction in rate was observed in the pH range 3–7, indicating a substrate inhibition of the *Thielavia terrestris* glucoamylase (FIG. 4). FIG. 5A shows the pH profiles of the activity corresponding to 0.25 and 0.50 mM maltotriose, a concentration range where the maltotriose inhibition was insignificant. Both profiles showed a pH optimum at 4. The K$_m$ and V$_{max}$ were calculated over the maltotriose concentration ranges where no substrate inhibition took place. The pH dependence of K$_m$, k$_{cat}$, and k$_{cat}$/K$_m$ are shown in FIGS. 5B and 5C. Although k$_{cat}$/K$_m$ became optimal at pH 4, k$_{cat}$ reached the highest value at pH 5.

Figure 8A:
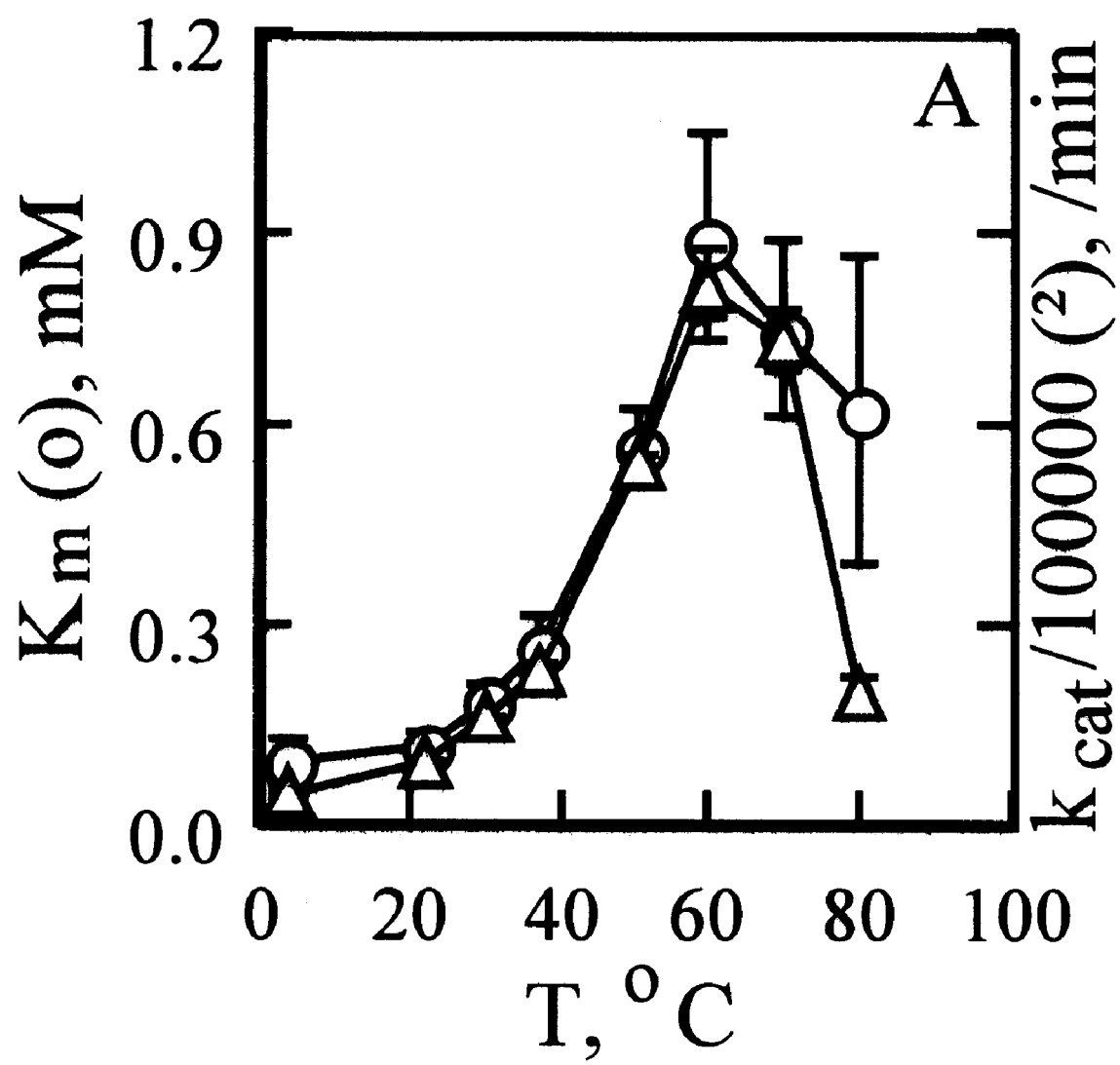
FIG. 8 shows the thermal profiles for a *Thielavia terrestris* ATCC 20627 glucoamylase. (A) $K_m$ (o), $k_{cat}$ (Δ). (B) $\log(k_{cat}/K_m)$ (unit: $M^{-1}min^{-1}$). (C) $\ln(k_{cat}/K_m)$ (on the inverse of T; unit: K). Correlation lines: $\ln(k_{cat}/K_m)=26-2360/T$ (for 4–30° C.); $\ln(k_{cat}/K_m)=19-342/T$ (for 22° C. to 70° C.).
Figure 8B:
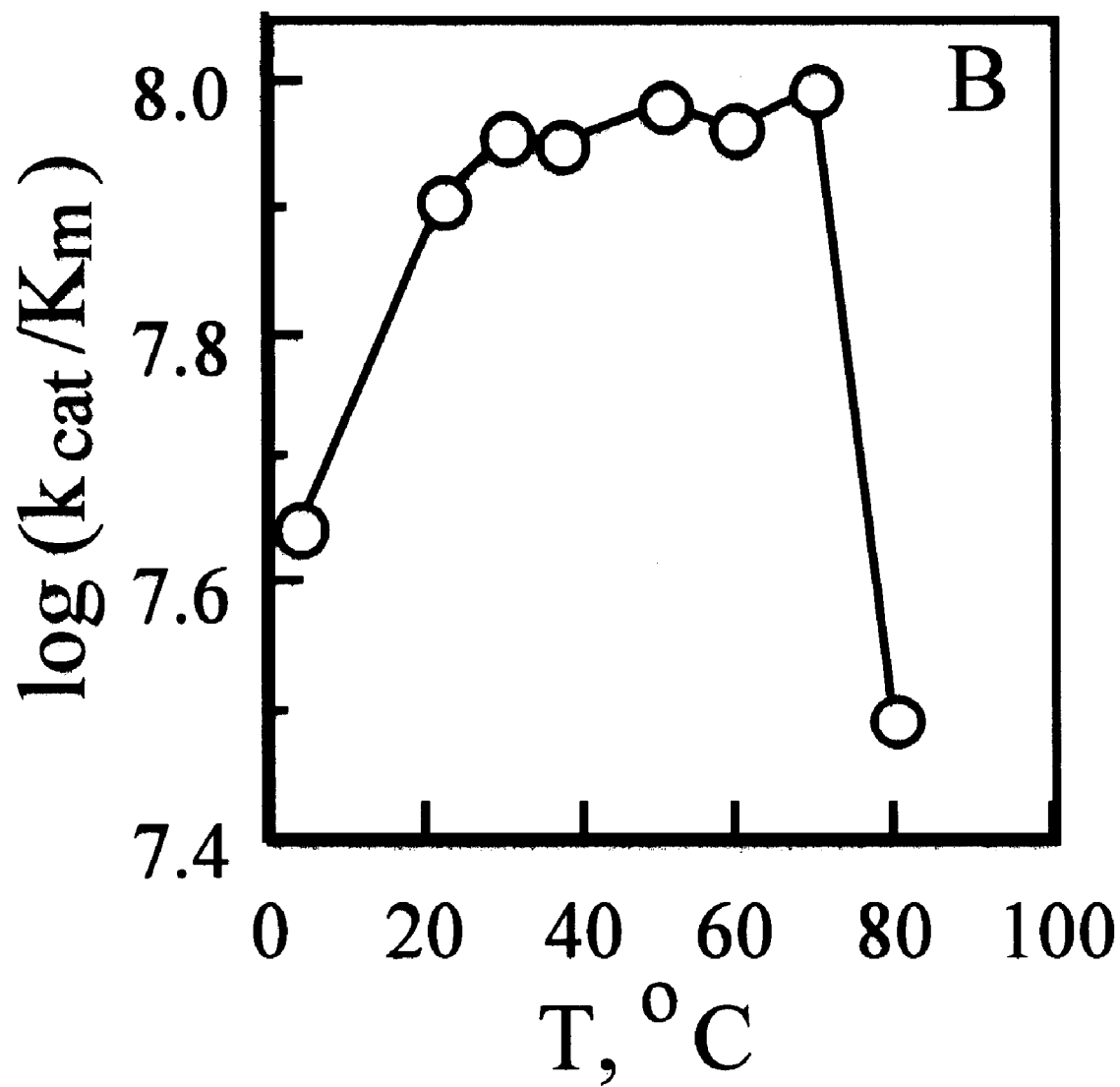
Figure 9A:
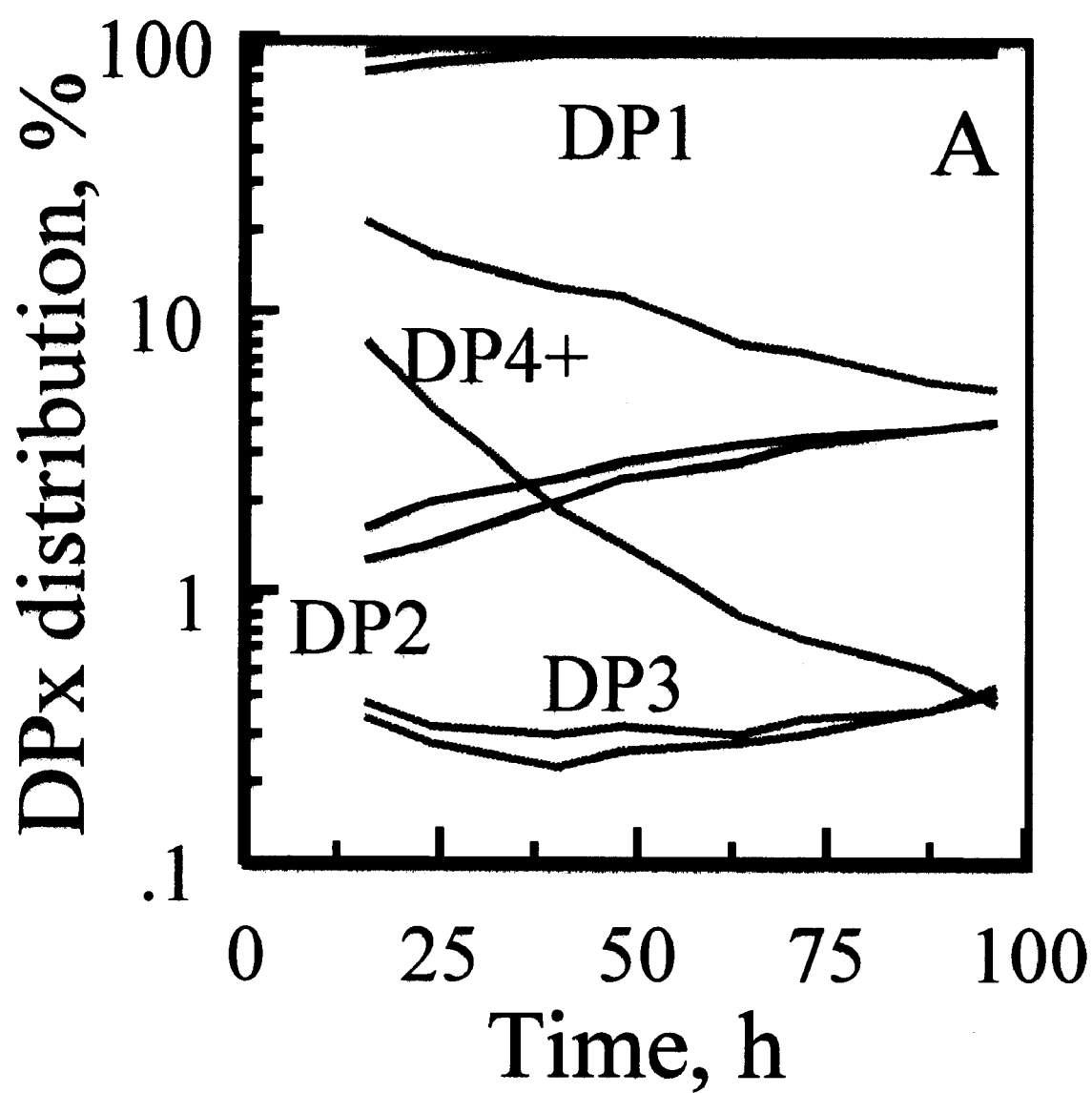
FIGS. 9A, B, and show the saccharification of maltodextrin by *Thielavia terrestris* glucoamylase at (A) 60° C., (B) 65° C., and (C) 70° C. Enzymes tested: solid line, *Thielavia terrestris* glucoamylase; dashed line, *Aspergillus niger* glucoamylase. Hydrolyzed product: DP1, glucose; DP2, maltose; DP3, maltotriose; DP4+, maltotetraose and longer maltooligomers.
Figure 9B:
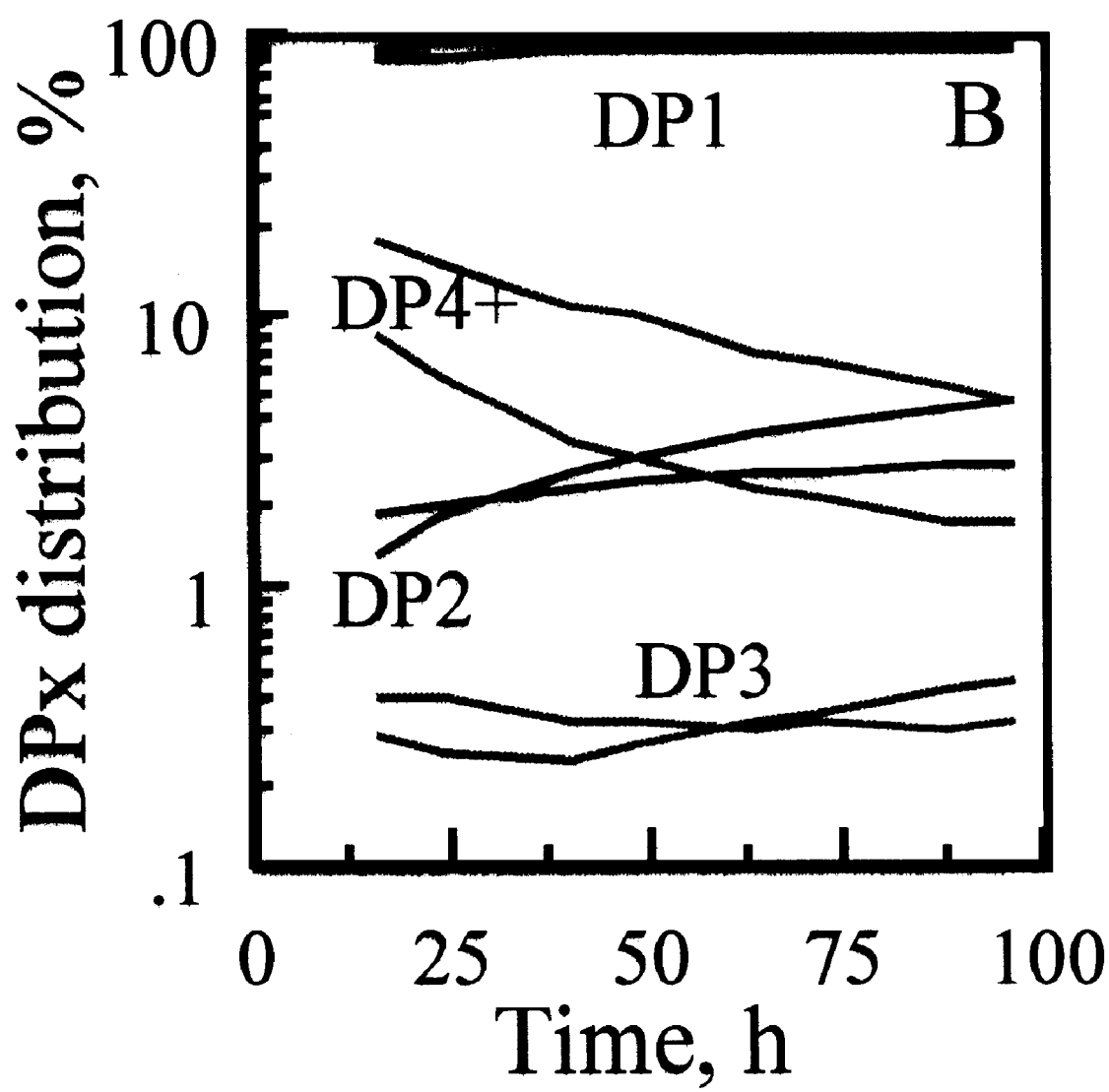
Figure 9C:
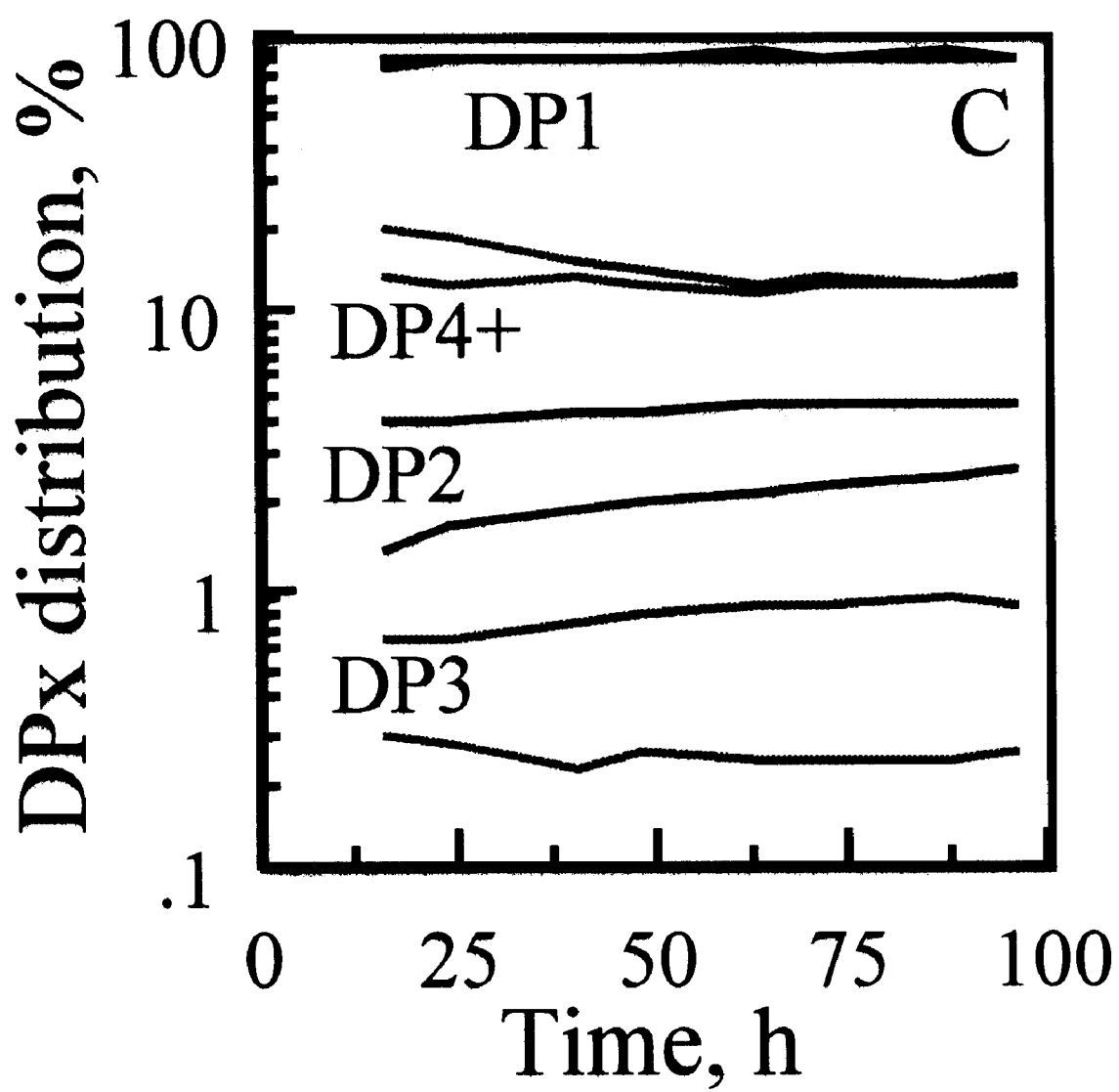

At high temperatures, *Thielavia terrestris* glucoamylase exhibited Michaelis rate-substrate concentration dependence (FIG. 8A). FIG. 8B shows the profile of the initial rate when the maltotriose concentration was 0.25 mM or 0.50 mM. A temperature optimum at 60–70° C. was observed. FIG. 9 shows the temperature dependence of K$_m$ and k$_{cat}$ extracted from the data obtained at a maltotriose concentration=5 mM (FIGS. 9A, 9B). Both parameters had a maximum at 60° C. The dependence of log($k_{cat}/K_m$) on the inverse of temperature in the range of 30–70° C. suggested an apparent activation free energy of 2.8 kJ/mol (FIG. 9C).

Thielavia terrestris glucoamylase had a $K_m$ of 0.33 mM for maltotriose at pH 4, which was smaller than the 0.45 of Aspergillus spp K-27 glucoamylase (Abe et al., 1990, Carbohydrate Res. 203: 129–138), 0.5 of Trichoderma reesei glucoamylase (Fagerström and Kalkkinen, 1995, Biotechnol. Appl. Biochem. 21: 223–231), and 0.73 of Aspergillus awamori glucoamylase (Sierks and Svensson, 1993, Biochemistry 32: 1113–1117); and a $k_{cat}$ of 5500 $min^{-1}$, which was higher than the 3900 of Aspergillus spp K-27 glucoamylase (Abe et al., 1990, Carbohydrate Res. 203: 129–138), 3700 of Aspergillus awamori glucoamylase (Sierks and Svensson, 1993, Biochemistry 32: 1113–1117), and 1200 of Trichoderma reesei glucoamylase (Fagerström and Kalkkinen, 1995, Biotechnol. Appl. Biochem. 21: 223–231).

Figure 8C:
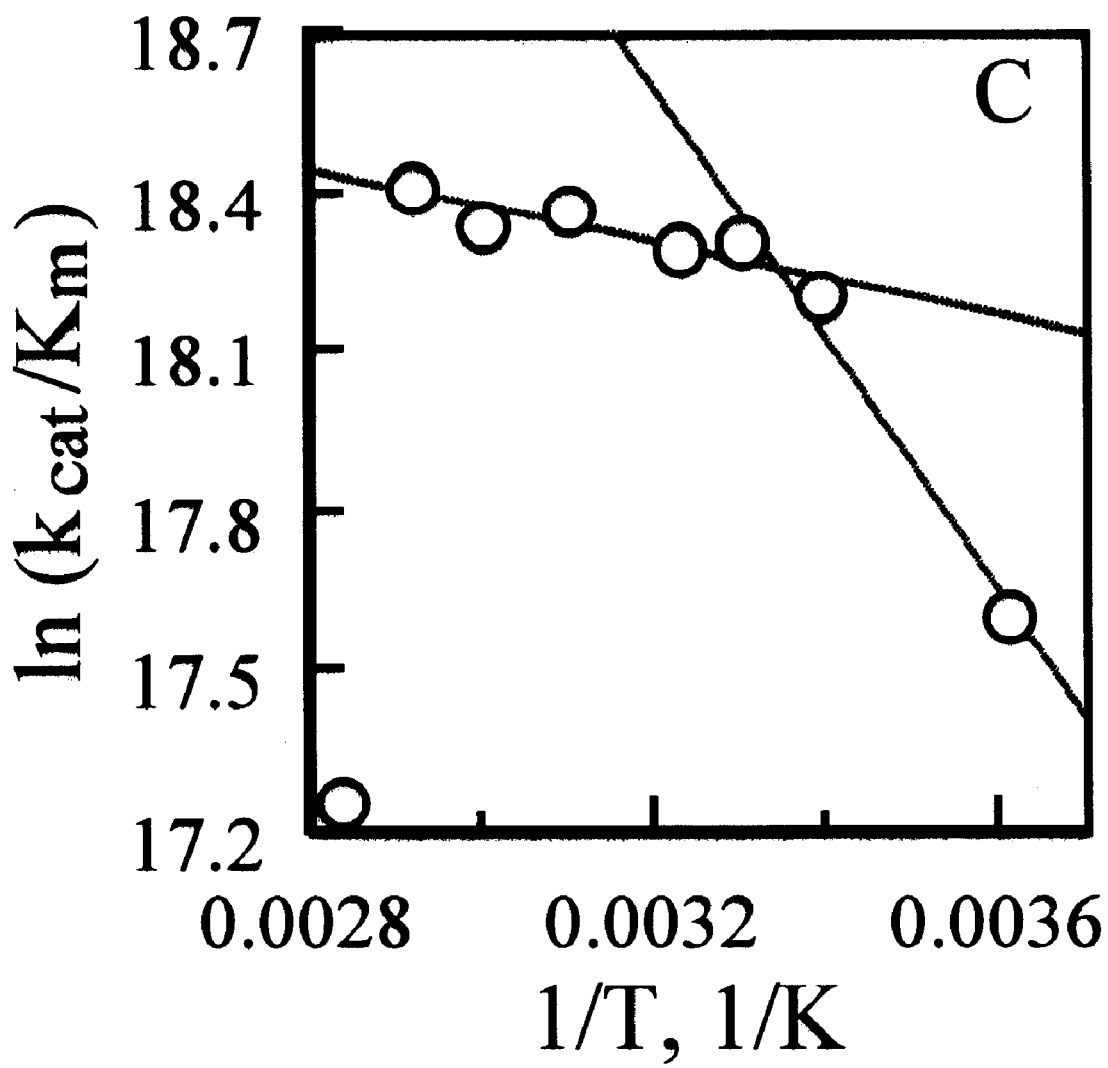

With maltotriose, Thielavia terrestris glucoamylase showed a $k_{cat}$ and $K_m$ that was maximal at pH 5 (FIG. 5). Thus the observed pH optimum of the Thielavia terrestris glucoamylase was a result of $k_{cat}/K_m$. These results showed that at pH 4 with maltotriose as substrate, both the $K_m$ and $k_{cat}$ of the Thielavia terrestris glucoamylase reached the maximum at 60° C. (FIG. 8).

Saccharification

The ability of the Thielavia terrestris glucoamylase to saccharify maltodextrin was evaluated relative to the Aspergillus niger glucoamylase The substrate for saccharification was made by dissolving 30% (w/w) maltodextrin (prepared from common corn) in boiling deionized water and the pH was adjusted to 4.5 at 60° C. Aliquots of substrate corresponding to 15 g dry solids were transferred to 50-ml glass flasks, mixed with enzyme (0.06–0.12 mg/g maltrodextrin), pH readjusted to 4.5 if necessary, and incubated in a water bath at temperatures of 60, 65, and 70° C. with stirring. Samples were taken periodically for carbohydrate analysis by HPLC. To inactivate the enzyme, the samples were first heated in boiling water for 15 minutes. The samples were then mixed with ion-exchange resin AG 501/X8(D) (Bio-Rad) for 30 minutes, filtered on a 0.2 μm filter, and analyzed by HPLC.

FIGS. 10A–C show the hydrolysis of maltodextrin by Thielavia terrestris glucoamylase in comparison with Aspergillus niger glucoamylase. Thielavia terrestris glucoamylase yielded 90% DP1 after 48 h, similar to that found with Aspergillus niger glucoamylase. Performance of Aspergillus niger glucoamylase generally dropped with temperature, showing increased levels of DP4$^+$ and decreased glucose levels. Using Thielavia terrestris glucoamylase more DP4$^+$ was produced at 65° C. than at 60° C., but the corresponding increase in product was mainly DP2, not DP1. The level of isomaltose produced by the Thielavia terrestris glucoamylase (62% isomaltose/maltose of total DP2 at 60° C.) was higher than that found using the Aspergillus niger glucoamylase (55%). The difference increased when the temperature reached 70° C. (50% versus 6% of total DP2).

DEPOSIT OF BIOLOGICAL MATERIAL

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| E. coli pEJG72/XL1Blue | NRRL B-30358 | October 27, 2000 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having glucoamylase activity, selected from the group consisting of:
   (a) a polypeptide having an amino acid sequence which has at least 90% identity with amino acids 20 to 630 of the mature polypeptide of SEQ ID NO:2;
   (b) a polypeptide which is encoded by a nucleic acid sequence which hybridizes under high stringency conditions with (i) nucleotides 411 to 2581 of SEQ ID NO:1, (ii) a fragment of (i) of at least 100 contiguous nucleotides, or (iii) a complementary strand of (i) or (ii), wherein high stringency conditions are defined as prehybridization and hybridizaton at 42° C. in 5× SSPE, 0.3% SDS, 200 µg/ml sheared and denatured salmon sperm DNA, and 50% formamide, and washing with 2×SSC, 0.2% SDS at 65° C.;
   (c) a fragment of (a) or (b), that has glucoamylase activity; and
   (d) a polypeptide obtained from Thielavia having glucoamylase activity with physicochemical properties of (i) a pH optimum in the range between about pH 3 and about pH 7. determined at 20° C. in the presence of maltotriose; (ii) a temperature optimum in the range of about 20° C. to about 70° C., determined at pH 4 in the presence of maltotriose, and (iii) a residual activity of 32%, relative to initial activity, at pH 4.3 after 20 minutes at 70° C. in the absence of maltotriose.

2. The polypeptide of claim 1, having an amino acid sequence which has at least 90% identity with amino acids 20 to 630 of SEQ ID NO:2.

3. The polypeptide of claim 2, having an amino acid sequence which has at least 95% identity with amino acids 20 to 630 of SEQ ID NO:2.

4. The polypeptide of claim 3, having an amino acid sequence which has at least 97% identity with amino acids 20 to 630 of SEQ ID NO:2.

5. The polypeptide of claim 1, comprising the amino acid sequence of SEQ ID NO:2.

6. The polypeptide of claim 1, consisting of the amino acid sequence of SEQ ID NO:2 or an enzymatically active fragment thereof.

7. The polypeptide of claim 6, consisting of the amino acid sequence of SEQ ID NO 2.

8. The polypeptide of claim 7, which consists of amino acids 20 to 630 of SEQ ID NO:2.

9. The polypeptide of claim 1, which is encoded by a nucleic acid sequence which hybridizes under high stringency conditions with (a) nucleotides 411 to 2581 of SEQ ID NO:1, (b) a fragment of (a) of at least 100 contiguous nucleotides, or (iii) a complementary strand of (a) or (b), wherein high stringency conditions are defined as prehybridization and hybridization at 42° C. in 5×SSPE, 0.3% SDS, 200 µg/ml sheared and denatured salmon sperm DNA, and 50% formamide, and washing with 2×SSC, 0.2% SDS at 65° C.

10. The polypeptide of claim 9, which is encoded by a nucleic acid sequence which hybridizes under high stringency conditions with (a) nucleotides 411 to 2581 of SEQ ID NO:1, or (b) a complementary strand of (a), wherein high stringency conditions are defined as prehybridization and hybridization at 42° C. in 5×SSPE 0.3% SDS, 200 µg/ml sheared and denatured salmon sperm DNA, and 50% formamide, and washing with 2×SSC, 0.2% SDS at 65° C.

11. The polypeptide of claim 1, with physicochemical properties of (a) a pH optimum in the range between about pH 3 and about pH 7, determined at 20° C. in the presence of maltotriose; (b) a temperature optimum in the range of about 20° C. to about 70° C., determined at pH 4 in the presence of maltotriose; and (c) a residual activity of 32%, relative to initial activity, at pH 4.3 after 20 minutes at 70° C. in the absence of maltotriose.

12. The polypeptide of claim 1, which is encoded by the nucleic acid sequence contained in plasmid pEJG72/XL1 Blue which is contained in *E. coli* NRRL B-30358.

* * * * *

SEQUENCE LISTING

<160> NUMBER OF SEQ ID NOS: 8

<210> SEQ ID NO 1
<211> LENGTH: 3196
<212> TYPE: DNA
<213> ORGANISM: Thielavia terrestris

<400> SEQUENCE: 1
tctagaagac ggtaccattg ccattcggcc cttcctaagc ggctggtcgg aataagcttt      60
cggcccccca cggataccc ataactatcc tgggccgaca tcatctgtac tccgaactcg     120

-continued

| | |
|---|---|
| acagactgct tatcggtcct ttatcccagg tcgcggggcc ccgcaggccg agtcggagcc | 180 |
| ggacggtgcc gcctccaggt ctcaccacaa gtggggatga actgcaacgg tcaggttgat | 240 |
| ggctccatat tcccccatat aaagacatcg tcgatctctc tcgagcttat ggcttccacg | 300 |
| cagcttcgca ccggccgtct caacttctgg cttgatcgtt ttccacgtcc agcatgcgcc | 360 |
| gtcttcagct cttgggctta ttggccctgc ttcctgctgc gctcggccat ccggaggcta | 420 |
| gccgtgtccg gcgcgagggg gaggtggtga agaggtctgt cgactccttc atcgccaccg | 480 |
| agagcccact tgccttgtcc aacctgctct gtaacatcgg ctcaactggc tgccatgctt | 540 |
| ctggcgtcgc ctcgggtatc gtcgttgcgt ccccggacaa gacgaacccg gactgtatgt | 600 |
| tgcactcggc ctctcttccc gccgctgttc gcaggctaac ttgtacagac tggtatactt | 660 |
| ggactagaga cagcgcgctc accttcaagt gcgttgtcga caccttcacc aacagctacg | 720 |
| atgcctcgct ccaggcggag atccagaact acatcgtcgc gcaggcccat ctgcagggcg | 780 |
| tctcgaaccc gtccggcagc ctctcggacg gttccggcct gggagaaccc aagttcaacg | 840 |
| tcgacatgag ccagttcacg ggcgcctggg gtatgtcttg caagcccacg cctcgacact | 900 |
| gtgtccccgt ttcattatcc tgaccagcaa caggtcgacc acagagagac ggtccggctc | 960 |
| tccgggcgat cgccctgatc gcttactcaa agtggctgat cagcaacggg tacacttcga | 1020 |
| ctgcgtcgag catcgtctgg cccgtcatca agaacgatct ggcatacgtt gcccagtact | 1080 |
| ggtgagctgc tgatccgaac cgtcaatgtg ctgagagggc gaccggctga cattcatccc | 1140 |
| tttcatacag gaacaacaca ggtttcgatc tttgggagga agtctctggc agttccttct | 1200 |
| tcacggtcgc caaccaacac agaggtacgg cggatatcaa agtgacaacc cactgacccg | 1260 |
| cctgctgacg tcgactggtg gcccgtagca ttggtggagg gtgccgccct tgccacgtcg | 1320 |
| ctcggtactt cttgcagtgc ctgctctgcc gtcgcgcccc agatcctgtg cttcctgcag | 1380 |
| agcttctggt cgccctccag cggctatatt ctcgccaaca gtacgtacat gcatcattca | 1440 |
| tatcgcacag tgcagggttg tcggtggtgc taacaaaaat caagtcaacg agaacaacgg | 1500 |
| ccgcagcgcc aaggacgcga acacattgct gggctcgatt cacacgtttg atcccgccgc | 1560 |
| gggctgcgac gcggcgactt tccagccctg cagtgaccgg gcgctggcca accacaaggt | 1620 |
| cgtgaccgac gcgttccggt ccatctactc catcaactcc ggcattgccg agggcagcgc | 1680 |
| cgtcgcggtc ggccgctatc ccgaggacag ctacttcggc ggcaaccccct ggtacctcaa | 1740 |
| cacactggcc gccgccgagc agctgtacga tgccctctac gtctggaaga agcagggctc | 1800 |
| catcaccgtc acatcgacgt cgctggcctt cttcaaagac ttctcgtcgt ccatcacccc | 1860 |
| gggcacgtac tcctccagca gtcgacgta cacaaccctg tacaacgcca tctcggcgta | 1920 |
| cgccgacggc tacatgaaca tcgtcgccca gtacgcgcag accaacggct cgctgtcgga | 1980 |
| gcagttctcc aagaccaacg cgcagccgct ctccgcctac gacctgacct ggtcctacgc | 2040 |
| ggccttcctc acggcagcgg cccgccgcgc cggcgtcgtg ccccctcct ggggcgccgc | 2100 |
| ctcggccaac agcgtcccgg cgcagtgctc cgccacctcc gtcgtcggct cctacacctc | 2160 |
| cgcgaccgcg acctccttcc cgccgtcgca gaccccggca tccagcacct ccgccggctc | 2220 |
| cagcccgct tcttccacca ccgccaccgc caccgcctgc tccacccga ccgccgtcgc | 2280 |
| cgtcaccttc aacgagcgcg tgaccaccca gtggggccag acgatcaagg tggtcggcga | 2340 |
| cgcggccgcg ctcggcggct gggacaccag caaggccgtg ccgctcagcg ccgccggcta | 2400 |
| caccgccagc gacccgctgt ggtcgggcac cgtcgacctg cccgccggcc tggccgtgca | 2460 |
| gtacaagtac atcaacgtgg cggccgacgg gggcgtcacg tgggaggcgg atccgaatca | 2520 |

-continued

```
ttcgtttacg gtgccggctg cgtgcgggac cacggcggta accaggatgg ataccggca     2580 gtaaattcga ggatgggttg gggagggtgg tggtgggagg ttgtttgggt gcggcggtgg     2640
gatgggatgt agggttgaat gggaggtggc ccaagcaagt ggtcaacgta cgctattctg     2700
atgacgattt ggattcttct gtatatagtt cttatgaagt tgtatgtact tgacatgaat     2760
aacgatgatg tccttgcttc aatatgcatt ctgctcggga gttgaaaatt agttcatgct     2820
tcatattggt ggccattgat tcgaacgaag acctgacgcc catgacgttg gcctcaatca     2880 cttcatatc ggcaagagaa tcgatagggg agccgctggc gtattgtacc cgccaagaaa     2940
cccctttctc ccacttcgtc accatcaaga gcctcctccg ccctggactt tgccgtcgac     3000
gaggactcag ggatgcagct tacaccccgc acatggctcc ggcggcagca cgctctggta     3060
gacatcctcc cgcggcttcc cggagacatt caagtacccg acggcgccct tatccaaccg     3120
aaagatggcg tggtccacca gcgcgtaggt gccgggcacg atcatctcca tatccacgat     3180
ggtcgccgcg cccggg                                                     3196
```

<210> SEQ ID NO 2
<211> LENGTH: 630
<212> TYPE: PRT
<213> ORGANISM: Thielavia terrestris

<400> SEQUENCE: 2

```
Met Arg Arg Leu Gln Leu Leu Gly Leu Leu Ala Leu Leu Pro Ala Ala
  1               5                  10                  15

Leu Gly His Pro Glu Ala Ser Arg Val Arg Arg Glu Gly Glu Val Val
                 20                  25                  30

Lys Arg Ser Val Asp Ser Phe Ile Ala Thr Glu Ser Pro Ile Ala Leu
             35                  40                  45

Ser Asn Leu Leu Cys Asn Ile Gly Ser Thr Gly Cys His Ala Ser Gly
         50                  55                  60

Val Ala Ser Gly Ile Val Val Ala Ser Pro Asp Lys Thr Asn Pro Asp
 65                  70                  75                  80

Tyr Trp Tyr Thr Trp Thr Arg Asp Ser Ala Leu Thr Phe Lys Cys Val
                 85                  90                  95

Val Asp Thr Phe Thr Asn Ser Tyr Asp Ala Ser Leu Gln Ala Glu Ile
                100                 105                 110

Gln Asn Tyr Ile Val Ala Gln Ala His Leu Gln Gly Val Ser Asn Pro
            115                 120                 125

Ser Gly Ser Leu Ser Asp Gly Ser Gly Leu Gly Glu Pro Lys Phe Asn
        130                 135                 140

Val Asp Met Ser Gln Phe Thr Gly Ala Trp Gly Arg Pro Gln Arg Asp
145                 150                 155                 160

Gly Pro Ala Leu Arg Ala Ile Ala Leu Ile Ala Tyr Ser Lys Trp Leu
                165                 170                 175

Ile Ser Asn Gly Tyr Thr Ser Thr Ala Ser Ser Ile Val Trp Pro Val
            180                 185                 190

Ile Lys Asn Asp Leu Ala Tyr Val Ala Gln Asn Asn Thr Gly Phe Asp
        195                 200                 205

Leu Trp Glu Glu Val Ser Gly Ser Ser Phe Phe Thr Val Ala Asn Gln
    210                 215                 220

His Arg Ala Leu Val Glu Gly Ala Ala Leu Ala Thr Ser Leu Gly Thr
225                 230                 235                 240

Ser Cys Ser Ala Cys Ser Ala Val Ala Pro Gln Ile Leu Cys Phe Leu
```

-continued

```
                245                 250                 255
Gln Ser Phe Trp Ser Pro Ser Gly Tyr Ile Leu Ala Asn Ser Thr
            260                 265                 270
Ala Lys Asp Ala Asn Thr Leu Leu Gly Ser Ile His Thr Phe Asp Pro
            275                 280                 285
Ala Ala Gly Cys Asp Ala Ala Thr Phe Gln Pro Cys Ser Asp Arg Ala
            290                 295                 300
Leu Ala Asn His Lys Val Val Thr Asp Ala Phe Arg Ser Ile Tyr Ser
305                 310                 315                 320
Ile Asn Ser Gly Ile Ala Glu Gly Ser Ala Val Ala Val Gly Arg Tyr
                325                 330                 335
Pro Glu Asp Ser Tyr Phe Gly Gly Asn Pro Trp Tyr Leu Asn Thr Leu
            340                 345                 350
Ala Ala Ala Glu Gln Leu Tyr Asp Ala Leu Tyr Val Trp Lys Lys Gln
            355                 360                 365
Gly Ser Ile Thr Val Thr Ser Thr Ser Leu Ala Phe Phe Lys Asp Phe
            370                 375                 380
Ser Ser Ser Ile Thr Pro Gly Thr Tyr Ser Ser Thr Ser Thr Tyr
385                 390                 395                 400
Thr Thr Leu Tyr Asn Ala Ile Ser Ala Tyr Ala Asp Gly Tyr Met Asn
                405                 410                 415
Ile Val Ala Gln Tyr Ala Gln Thr Asn Gly Ser Leu Ser Glu Gln Phe
            420                 425                 430
Ser Lys Thr Asn Gly Glu Pro Leu Ser Ala Tyr Asp Leu Thr Trp Ser
            435                 440                 445
Tyr Ala Ala Phe Leu Thr Ala Ala Ala Arg Arg Ala Gly Val Val Pro
            450                 455                 460
Pro Ser Trp Gly Ala Ala Ser Ala Asn Ser Val Pro Ala Gln Cys Ser
465                 470                 475                 480
Ala Thr Ser Val Val Gly Ser Tyr Thr Ser Ala Thr Ala Thr Ser Phe
                485                 490                 495
Pro Pro Ser Gln Thr Pro Ala Ser Thr Ser Ala Gly Ser Ser Pro
            500                 505                 510
Ala Ser Ser Thr Thr Ala Thr Ala Thr Ala Cys Ser Thr Pro Thr Ala
            515                 520                 525
Val Ala Val Thr Phe Asn Glu Arg Val Thr Thr Gln Trp Gly Gln Thr
            530                 535                 540
Ile Lys Val Val Gly Asp Ala Ala Leu Gly Gly Trp Asp Thr Ser
545                 550                 555                 560
Lys Ala Val Pro Leu Ser Ala Ala Gly Tyr Thr Ala Ser Asp Pro Leu
                565                 570                 575
Trp Ser Gly Thr Val Asp Leu Pro Ala Gly Leu Ala Val Gln Tyr Lys
            580                 585                 590
Tyr Ile Asn Val Ala Ala Asp Gly Gly Val Thr Trp Glu Ala Asp Pro
            595                 600                 605
Asn His Ser Phe Thr Val Pro Ala Ala Cys Gly Thr Thr Ala Val Thr
            610                 615                 620
Arg Asp Asp Thr Trp Gln
625                 630

<210> SEQ ID NO 3
<211> LENGTH: 24
<212> TYPE: DNA
<213> ORGANISM: Thielavia terrestris
```

-continued

<400> SEQUENCE: 3
gtcgactcgt atatccagac cgag                                                          24

<210> SEQ ID NO 4
<211> LENGTH: 24
<212> TYPE: DNA
<213> ORGANISM: Thielavia terrestris

<400> SEQUENCE: 4
gaggtaccac gggttaccgt tgta                                                          24

<210> SEQ ID NO 5
<211> LENGTH: 24
<212> TYPE: DNA
<213> ORGANISM: Thielavia terrestris

<400> SEQUENCE: 5
atgatgcgcc gtcttcagct cttg                                                          24

<210> SEQ ID NO 6
<211> LENGTH: 26
<212> TYPE: DNA
<213> ORGANISM: Thielavia terrestris

<400> SEQUENCE: 6
gggttaatta attactgcca ggtatc                                                        26

<210> SEQ ID NO 7
<211> LENGTH: 24
<212> TYPE: DNA
<213> ORGANISM: Thielavia terrestris

<400> SEQUENCE: 7
atgatgcgcc gtcttcagct cttg                                                          24

<210> SEQ ID NO 8
<211> LENGTH: 24
<212> TYPE: DNA
<213> ORGANISM: Thielavia terrestris

<400> SEQUENCE: 8
gggatgcatt tactgccagg tatc                                                          24